US008267887B2

(12) United States Patent
Mohl

(10) Patent No.: US 8,267,887 B2
(45) Date of Patent: Sep. 18, 2012

(54) TREATING HEART TISSUE

(75) Inventor: Werner Mohl, Altenmarkt-Thennenberg (AT)

(73) Assignee: Miracor Medical Systems GmbH, Vienna (AT)

( * ) Notice: Subject to any disclaimer, the term of this patent is extended or adjusted under 35 U.S.C. 154(b) by 58 days.

(21) Appl. No.: 12/788,016

(22) Filed: May 26, 2010

(65) Prior Publication Data
US 2011/0295177 A1  Dec. 1, 2011

(51) Int. Cl.
*A61M 29/00* (2006.01)
(52) U.S. Cl. ............ 604/102.02; 604/102.01; 604/96.01
(58) Field of Classification Search ............... 604/96.01, 604/97.01, 102.01–102.03
See application file for complete search history.

(56) References Cited

U.S. PATENT DOCUMENTS

| | | |
|---|---|---|
| 4,589,869 A | 5/1986 | Wernborg |
| 4,657,536 A | 4/1987 | Dorman |
| 4,671,796 A | 6/1987 | Groshong et al. |
| 4,701,166 A | 10/1987 | Groshong et al. |
| 4,705,501 A | 11/1987 | Wigness et al. |
| 4,887,608 A | 12/1989 | Mohl et al. |
| 4,934,996 A | 6/1990 | Mohl et al. |
| 4,943,277 A | 7/1990 | Bolling |
| 4,969,470 A | 11/1990 | Mohl et al. |
| 5,156,600 A | 10/1992 | Young |
| 5,224,938 A | 7/1993 | Fenton, Jr. |
| 5,226,427 A | 7/1993 | Buckberg et al. |
| 5,466,216 A | 11/1995 | Brown et al. |
| 5,707,358 A | 1/1998 | Wright |
| 5,755,686 A | 5/1998 | O'Neill et al. |
| 5,779,685 A | 7/1998 | Thompson et al. |
| 6,461,327 B1 * | 10/2002 | Addis et al. ............... 604/101.04 |
| 6,500,145 B1 * | 12/2002 | Bicakci et al. ............. 604/96.01 |
| 6,506,146 B1 | 1/2003 | Mohl et al. |
| 6,569,145 B1 * | 5/2003 | Shmulewitz et al. ......... 604/509 |
| 6,786,888 B1 * | 9/2004 | Zadno-Azizi et al. ..... 604/99.02 |
| 7,331,922 B2 | 2/2008 | Mohl et al. |
| 2001/0020160 A1 * | 9/2001 | Esch et al. .................... 604/509 |
| 2001/0041863 A1 * | 11/2001 | Sweezer .................. 604/101.03 |
| 2002/0032359 A1 * | 3/2002 | Geoffrion et al. ................. 600/3 |

(Continued)

OTHER PUBLICATIONS

'Letters to the Editor: A New Technique for Pulmonary Arterial Catheter Insertion into Coronary Sinus Using Transesophageal Echocardiography' [online]. International Anesthesia Research Society, 2003 [retrieved May 27, 2010]. Retrieved from the Internet: <URL: http://www.anesthesia-analgesia.org/content/97/1/298.full.pdf>.

(Continued)

*Primary Examiner* — Victoria P Shumate
(74) *Attorney, Agent, or Firm* — Fish & Richardson P.C.

(57) ABSTRACT

Some embodiments of a system or method for treating heart tissue can include a catheter device that provides a user with the ability to perform a number of heart treatment tasks (before, during, and after a cardiac surgery or a percutaneous coronary intervention). In particular embodiments, the catheter device can be used to (i) precondition heart muscle tissue before the heart is isolated from the circulatory system, (ii) deliver cardioplegia into the coronary sinus during the cardiac surgery when the heart is isolated from the circulatory system, and (iii) control the blood flow through the heart after the heart is reconnected with the circulatory system. In some embodiments, the catheter device can perform some or all of: (i) intermittently occluding the coronary sinus, (ii) delivering a treatment fluid into the coronary sinus, and (iii) monitoring a flow rate of blood passing from the coronary sinus to the right atrium.

27 Claims, 10 Drawing Sheets

U.S. PATENT DOCUMENTS

| | | | |
|---|---|---|---|
| 2002/0120232 A1* | 8/2002 | Stumpp et al. | 604/95.03 |
| 2002/0133117 A1* | 9/2002 | Zadno-Azizi et al. | 604/99.04 |
| 2006/0200191 A1* | 9/2006 | Zadno-Azizi | 606/200 |
| 2008/0015404 A1* | 1/2008 | Mohl | 600/16 |
| 2008/0119742 A1* | 5/2008 | Mohl | 600/486 |
| 2010/0056849 A1 | 3/2010 | Mohl | |
| 2010/0130810 A1 | 5/2010 | Mohl | |

OTHER PUBLICATIONS

'Global Myocardial Protection' [online] Edwards Lifesciences, 2004 [retrieved May 27, 2010]. Retrieved from the Internet: <URL: http://ht.edwards.com/resourcegallery/products/cannulae/images/ar00519.pdf>.

'Myocardial Protection System' [online] Quest Medical, Inc. 2010 [retrieved May 27, 2010]. Retrieved from the Internet: <URL: http://www.questmedical.com/products/mps.asp>.

'Cardioplegia Delivery' [online] Quest Medical, Inc. 2010 [retrieved May 27, 2010]. Retrieved from the Internet: <URL: http://www.questmedical.com/products/cardio_catheters.asp>.

'Cannulation' [online] Medtronic, Inc. 2010 [retrieved May 27, 2010]. Retrieved from the Internet: <URL: hitp://www.medtronic.com/for-healthcare-professionals/products-therapies/cardiovascular/therapies/cannulation/index.htm>.

'MiRCSP Cannulae' [online]. Medtronic, Inc. 2010 [retrieved May 27, 2010]. Retrieved from the Internet: <URL: http://www.medtronic.com/for-healthcare-professionals/products-therapies/cardiovascular/cannulae-products/mircsp-cannula/index.htm>.

'Retrograde Perfusion Cannulae' [online]. Medtronic, Inc. 2010 [retrieved May 27, 2010]. Retrieved from the Internet: <URL: http://www.medtronic.com/for-healthcare-professionals/products-therapies/cadiovascular/cannulae-products/retrograde-perfusion-cannulae/index.htm>.

'Performer CPB' [online]. Medtronic, Inc. 2007 [retrieved May 27, 2010]. Retrieved from the Internet: <URL: http://www.medtronic.com/cardsurgery/arrested_heart/downloads/200704933.pdf>.

Mohl, Werner et al., "The legacy of coronary sinus interventions: Endogenous cardioprotection and regeneration beyond stem cell research." The American Association for Thoracic Surgery, 2008. The Journal of Thoracic and Cardiovascular Surgery, vol. 136, No. 5, pp. 1131-1135.

Mohl, Werner et al., "Is activation of coronary venous cells the key to cardiac regeneration?" Macmillan Publishers Ltd., 2008. Nature Clinical Practice, Cardiovascular Medicine, vol. 5, No. 9, pp. 528-530.

Onorati et al., "Coronary Sinus Perfusion Reverses Ongoing Myocardial Damage in Acute Ischemia." Wiley Periodicals, Inc. 2009. Journal compilation, International Center for Artificial Organs and Transplantation and Wiley Periodicals, Inc., 33 (10), pp. 788-797.

Mohl, Werner et al. "Coronary Sinus Library, ICSO and PICSO" Society of Coronary Sinus Interventions, 2003. A. Holzhausens Nfg., Austria.

* cited by examiner

Out Flow

TREATING HEART TISSUE

TECHNICAL FIELD

This document relates to systems and methods that are configured to treat heart tissue, for example, during an open heart surgical operation or during a percutaneous coronary intervention.

BACKGROUND

During some cardiac surgeries, the heart can be isolated from the circulatory system while the patient is connected to a heart-lung machine (also known as a perfusion machine). The heart-lung machine provides an extracorporeal circuit to oxygenate and pump blood through the patient's circulatory system. Typically, a venous catheter is inserted into the right atrium and drains blood returning from the body into the extracorporeal circuit of the heart-lung machine. Also, an arterial cannula is inserted into the aorta, so that oxygenated blood from the heart-lung machine can be pumped back into the patient's circulatory system. After these catheters are in place, the aorta may be cross clamped between the arterial cannula and the heart to thereby prevent blood from flowing backwards into the heart. Such a procedure provides oxygenated blood to all areas of the body except the heart. In order to prevent degradation of the heart muscle tissue during the surgery, a cold cardioplegic fluid can be infused into the heart to both cool the heart and stop it from beating. After the initial infusion, the heart may be periodically reperfused to maintain the reduced-temperature, dormant state of the heart.

The cardioplegia solution may be administered in an antegrade manner (through arteries in the normal direction of blood flow), in a retrograde manner (through veins opposite the normal blood flow direction), or in a combination of retrograde and antegrade administration. The cardioplegic solutions can temporarily stop the heart by interfering with the conduction of the heart's natural electric signals that cause heat beats.

Retrograde cardioplegia is conventionally administered by inserting a balloon catheter into the coronary sinus, inflating the balloon, and perfusing the cardioplegic solution backwards through the coronary veins. Some catheters for retrograde coronary sinus perfusion (RCSP) may employ a manually inflating balloon that is filled through an inflation lumen. While the balloon is inflated, the flow of blood or solution from the coronary sinus to the right atrium is blocked.

During the period of time that the heart is deprived of normal blood flow, there is a risk that a portion of the heart muscle tissue may be damaged (such as ischemic heart muscle tissue). Further, after the cardiac surgery in completed and the aorta is unclamped to restore normal blood flow to the heart, the immediate rush of blood through the heart muscle tissue can cause additional damage to the heart muscle tissue to a point that normal blood flow does not return through the ischemic portion of the heart muscle tissue.

Further, in some cases, the heart may be treated without the need for an external blood pump of a heart-lung machine. For example, during a percutaneous coronary intervention, a blockage in a coronary artery may be repaired or removed with a stent or angioplasty balloon that is percutaneously delivered. The blockage in the coronary artery can result in a loss of blood flow through a portion of the heart muscle tissue, thereby creating an area of damaged or ischemic heart muscle tissue.

SUMMARY

Some embodiments of a system or method for treating heart tissue can include a multi-functional catheter device that serves to protect or restore heart muscle tissue from damage during an open heart surgery (in combination with a heart-lung machine), an off-pump cardiac surgery, or a percutaneous coronary intervention procedures. The catheter device can be used, for example, in a process that intermittently occludes the coronary sinus, delivers cardioplegia or blood into the coronary sinus, or a combination thereof.

Particular embodiments described herein include of a system of method that provides a surgeon or other user with the ability to perform a number of heart treatment tasks (before, during, and after cardiac surgery) while a balloon device remains inflated in the coronary sinus. In particular, the catheter device can be readily used to precondition heart muscle tissue (locally) before the heart is isolated (or clamped) from the circulatory system. For example, the catheter device can be equipped to provide pressure-controlled intermittent coronary sinus occlusion (PICSO) treatment to the heart so as to precondition the heart muscle tissue with redistributed venous blood flow. Also, the catheter device can be employed to deliver cardioplegia (e.g., pulsatile retrograde cardioplegia in particular embodiments) into the coronary sinus during the cardiac surgery when the heart is isolated from the circulatory system. The pulsatile cardioplegia delivery can be used to dose the cardioplegia into the coronary sinus in an amount that is at least partially based upon pressure measurements in the coronary sinus. Furthermore, the catheter device can be employed to control the blood flow through the heart after the heart is reconnected (unclamped) with the circulatory system. As such, the initial blood flow though the heart muscle tissue can be limited in a controlled manner that reduces the likelihood of reperfusion injury to the heart muscle tissue that might otherwise occur if full normal blood flow was immediately restored. Such treatment tasks provided by the catheter while the balloon is inflated in the coronary sinus can lead to improved heart muscle tissue recovery after the cardiac surgery is completed and arterial blood flow returns to the heart muscle tissue.

In other embodiments, the catheter system described herein can be employed in an off-pump cardiac surgery in which the heart itself is providing the circulation (e.g., not a blood pump of a heart-lung machine). In such circumstances, the catheter device can be positioned in the coronary sinus to provide PICSO treatment to the heart. Further, the catheter device can include a lumen that selectively delivers retroperfusion blood into the coronary sinus (e.g., in the event of a sudden reduction in coronary sinus pressure). The blood delivered into the coronary sinus may comprise arterial blood that is sampled from a major artery or an external source of oxygenated blood. Such a process can be useful, for example, in cardiac surgeries when the heart is lifted in a pericardial cradle to allow surgical access to the posterior aspect of the heart (e.g., during coronary artery bypass in an off-pump cardiac surgery, or the like).

In alternative embodiments, the catheter system described herein can be used in a percutaneous coronary intervention (PCI) procedure. In such circumstances, the catheter device may be delivered percutaneously through the venous system and into the coronary sinus. The catheter device can provide PICSO treatment to the heart during the PCI procedure that is occurring in a different region of the heart. Also, the catheter device can include a lumen that selectively delivers retroperfusion blood into the coronary sinus (e.g., during a PCI procedure in which a longer period of perfusion deficit may occur). As previously described, the blood delivered into the coronary sinus may comprise arterial blood that is sampled from a major artery or an external source of oxygenated blood.

In some embodiments, a coronary sinus occlusion catheter may include a distal tip portion including an inflatable balloon device configured to engage an interior wall of a coronary sinus when inflated. The catheter may also include a distal port arranged distally of the inflatable balloon device so that the distal port extends into the coronary sinus when the inflatable balloon device is inflated in the coronary sinus. The catheter may further include an outflow port arranged proximally of the inflatable balloon device so that the outflow port is in fluid communication with the right atrium when the inflatable balloon device is inflated in the coronary sinus. The distal tip portion may at least partially define a fluid flow path from the distal port to the outflow port. The catheter may also include an inner movable member positioned in the flow path from the distal port to the outflow port. The inner movable member may be adjusted between a first position in which the flow path from the distal port to the outflow port is occluded and a second position in which the flow path from the distal port to the outflow port is open.

Particular embodiments described herein may include a method of treating heart tissue during a cardiac surgery. The method may include, prior to isolating a heart from a circulatory system in the body, advancing distal tip portion of a coronary sinus occlusion catheter into the coronary sinus so that a stabilization balloon device of the coronary sinus occlusion catheter engages with an interior wall of the coronary sinus. The method may also include preconditioning heart muscle tissue by intermittently occluding the coronary sinus using the coronary sinus occlusion catheter to redistribute venous blood flow into the heart muscle tissue while the stabilization balloon device continuously remains in an inflated condition in the coronary sinus. The method may further include, after isolating the heart from the circulatory system in the body, delivering a cardioplegia solution through a lumen of the coronary sinus occlusion catheter and into the coronary sinus while the stabilization balloon device continuously remains in an inflated condition in the coronary sinus. The method may also include, after the heart is reconnected to the circulatory system in the body, intermittently occluding the coronary sinus using the coronary sinus occlusion catheter to redistribute venous blood flow into heart muscle tissue while the stabilization balloon device continuously remains in an inflated condition in the coronary sinus.

In some embodiments, a system for cardiac surgery may include a coronary sinus occlusion catheter and a heart-lung machine. The catheter may include a distal tip portion, a proximal hub portion, a stabilization balloon device positioned along the distal tip portion and configured engage an interior wall of a coronary sinus when in an inflated condition, and an inner movable member that is adjustable between a first position and a second position for pressure-controlled intermittent coronary sinus occlusion. The heart-lung machine may include a plurality of lines coupled to the proximal hub portion of the coronary sinus occlusion catheter, and a control system to control movement of the inner movable member of the coronary sinus occlusion catheter. The control system of the heart-lung machine may be used to adjust the inner movable member between the first position in which a flow path from the coronary sinus to a right atrium is occluded and the second position in which the flow path from the coronary sinus to the right atrium is open.

In particular embodiments, a coronary sinus occlusion catheter may include a distal tip portion including an inflatable balloon device configured to engage an interior wall of a coronary sinus when in an inflated condition. The catheter may also include a first pressure sensor lumen extending to a distal position that is distal of the inflatable balloon device for detecting a first pressure. The catheter may further include a second pressure sensor lumen extending to a proximal position that is proximal of the inflatable balloon device for detecting a second pressure. The first pressure sensor lumen and the second pressure sensor lumen may be positioned relative to one another such that a difference between the first pressure and the second pressure is indicative of a flow rate of blood passing along the distal tip portion from a region distal of the balloon device to a region proximal of the balloon device.

The details of one or more embodiments of the invention are set forth in the accompanying drawings and the description below. Other features, objects, and advantages of the invention will be apparent from the description and drawings, and from the claims.

DESCRIPTION OF DRAWINGS

Like reference symbols in the various drawings indicate like elements.

DETAILED DESCRIPTION

Figure 1:
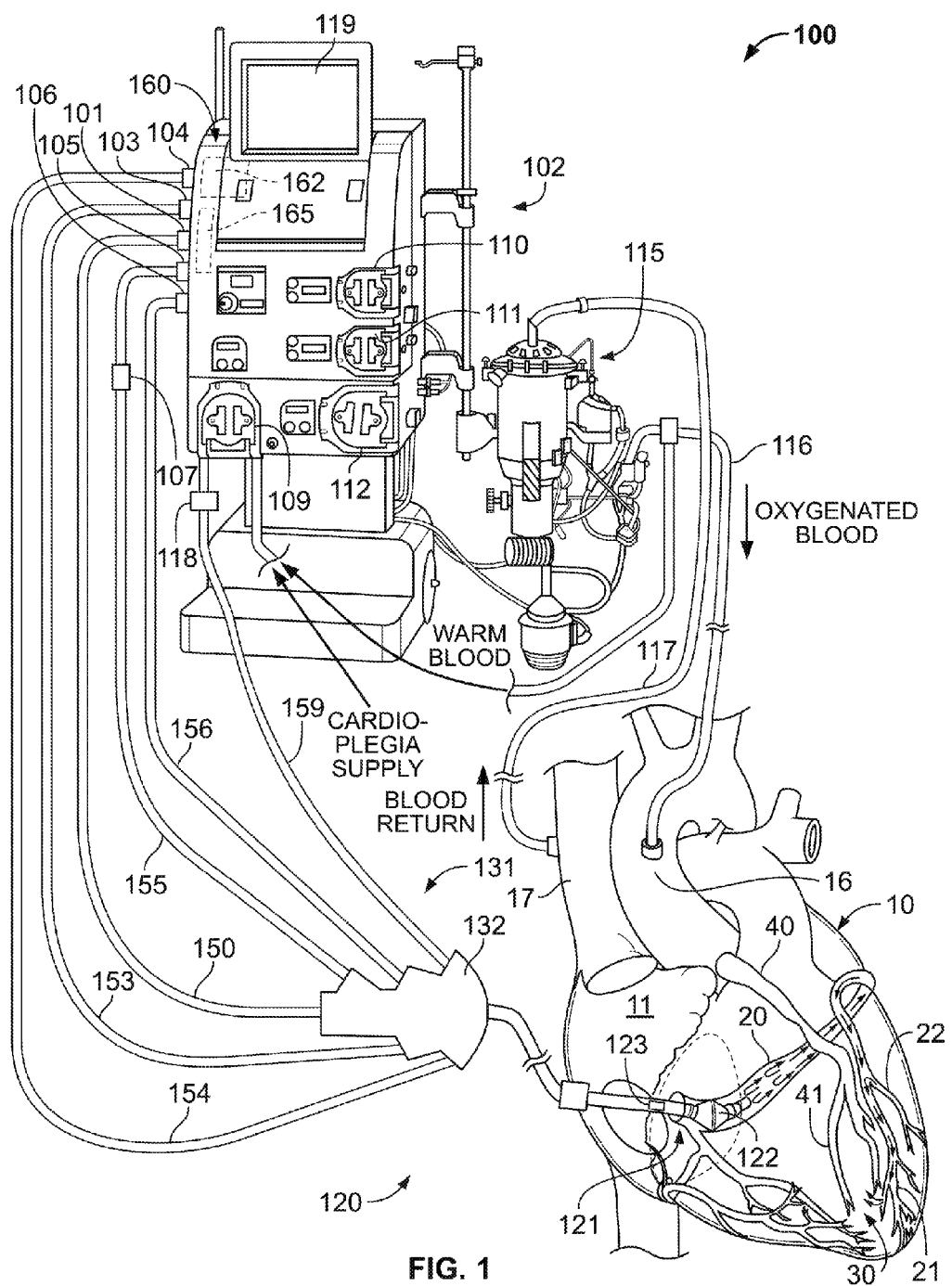
FIG. 1 is a perspective view of a system for treating heart tissue, in accordance with some embodiments.
Figure 2:
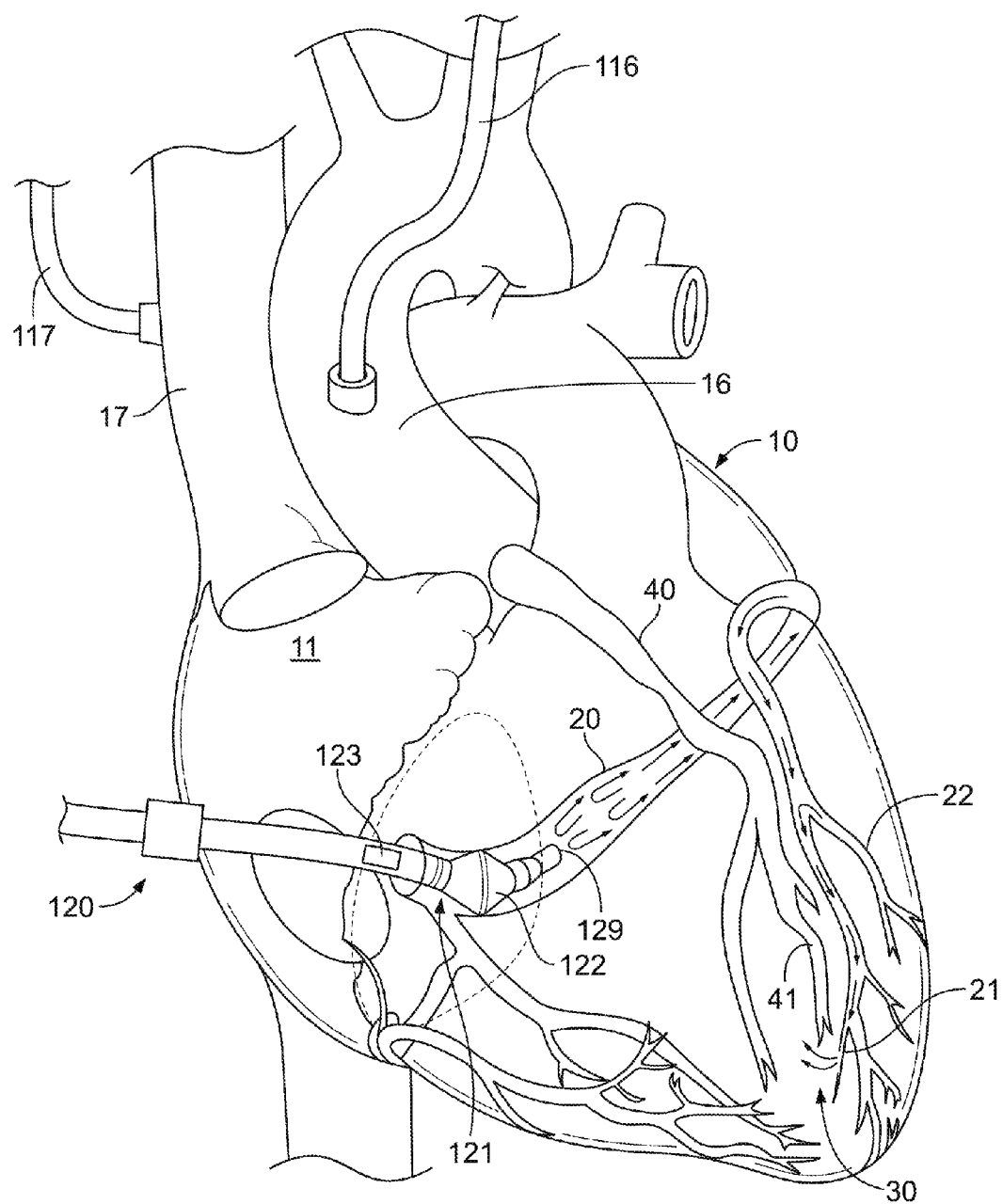
FIG. 2 is a perspective view of a portion of the system of FIG. 1.

Referring to FIGS. 1-2, some embodiments of a system 100 for treating heart tissue can include a coronary sinus occlusion catheter 120 and a heart-lung machine 102 (FIG. 1). The heart-lung machine 102 can operate as a perfusion system in which blood is oxygenated via an extracorporeal circuit during a cardiac surgery. As described in more detail below, the heart-lung machine 102 can house a catheter control system 160 that is configured to control the operation of the catheter 120 while a distal portion 121 of the catheter 120 is positioned in a vessel of the heart 10 (e.g., the coronary sinus 20 in the depicted embodiment). The coronary sinus occlusion catheter 120 includes the distal portion 121 (leading to a distal end depicted in FIG. 2) and a proximal portion 131, which includes a proximal hub 132 that is coupled to the heart-lung machine 102 via a number of fluid or sensor lines 150, 153, 154, 155, 156, and 159. Accordingly, the heart-lung machine 102 (including the catheter control system 160 housed therein) may be employed to operate one or more components at the distal tip portion 121 of the coronary sinus occlusion catheter 120 while also receiving one or more sensor signals that provide data indicative of heart characteristics (e.g., coronary sinus pressure, right atrium pressure of fluid flow, and the like).

Briefly, in use, the distal tip portion 121 of the coronary sinus occlusion catheter 120 can be arranged in a coronary sinus 20 of a heart 10 as part of a cardiac surgery in which the heart 10 will be isolated (e.g., clamped off) from the circulatory system. The catheter 120 can be advantageously employed to perform a number of functions before, during, and/or after the primary cardiac surgery (e.g., heart valve replacement, coronary bypass, or the like)—some or all of which can be performed while a balloon device 122 of the catheter 120 remains inflated in the coronary sinus 20. For instance, the catheter 120 can be readily used to precondition heart muscle tissue before the heart is isolated (or clamped off) from the circulatory system by providing PICSO treatment to the heart 10 so as to precondition the heart muscle tissue with redistributed venous blood flow. When the catheter 120 is activated to intermittently occlude the blood flow exiting from the coronary sinus 20 and into the right atrium 11, the venous blood flow that is normally exiting from the coronary sinus 20 may be redistributed into a portion of heart muscle tissue 30 to precondition or pre-treat that heart muscle tissue for the subsequent receipt of retrograde cardioplegia. Thus, while the portion of heart muscle tissue 30 normally receives blood flow from a coronary artery 40 and a local artery 41, the heart muscle tissue 30 will receive redistributed blood from the venous side (e.g., from the local vein 21 or other branch veins 22) while the coronary sinus 20 is intermittently occluded with the catheter 120. During a subsequent period of time in which the heart 10 is isolated from the circulatory system, the catheter 120 can be employed to deliver cardioplegia (e.g., pulsatile retrograde cardioplegia in particular embodiments) into the coronary sinus 20. The control system 160 housed in the heart-lung machine 102 can be configured to detect the pressure in the coronary sinus 20 and to thereafter determine an amount of cardioplegia that should be delivered through the catheter 120 and into the coronary sinus 20 based at least in part upon the pressure measurements of the coronary sinus 20. During yet another subsequent period of time in which the heart 10 is reconnected to the circulatory system (e.g., the clamp is removed to restore normal blood flow), the catheter 120 can control the blood flow through the heart 10 in order to limit any damage that might otherwise be caused during the initial reperfusion of normal blood flow through the heart muscle tissue.

Still referring to FIGS. 1-2, the control system 160 (FIG. 1) housed in the heart-lung machine 102 can be configured to provide automated control for both the inflatable balloon device 122 (which acts as a stabilization balloon in the coronary sinus 20) and an occlusion component (e.g., a movable inner member 140 (FIG. 3) of the catheter 120). As described in more detail below, the control system 160 includes control circuitry 162 having a computer processor (refer to FIG. 13) that executes computer-readable instructions stored on at least one computer memory device (refer to FIG. 13) so as to activate or deactivate the occlusion in the coronary sinus 20 in accordance with particular patterns. For instance, the control system 160 can be configured to activate the occlusion component of the catheter 120 in the coronary sinus 20 as part of a predetermined pattern of occlusion periods and release periods that is independent of the coronary sinus pressure, or as part of a pressure-dependent pattern that is at least partially defined by the coronary sinus pressure readings during the procedure. In addition, the heart-lung machine 102 is equipped with a display device 119 having a graphical user interface (e.g., a touch screen display device) that provides a surgeon or other user with time-sensitive, relevant data indicative of the progress of a coronary sinus occlusion procedure, a cardioplegia delivery procedure, and the condition of the heart 10. As such, the user can view the graphical user interface device 119 to readily monitor the heart's condition and the effects of (i) intermittently occluding the coronary sinus 20 or (ii) delivering cardioplegia to the coronary sinus 20.

The distal tip portion 121 of the coronary sinus occlusion catheter 120 can be delivered through the heart wall and positioned in the coronary sinus 20 so that the stabilization balloon 122 can be inflated in the coronary sinus 20. The stabilization balloon 122 can be position proximate to the ostium on the coronary sinus 120 so that a distal tip port 129 is located in the coronary sinus while an outflow port 123 is positioned in the right atrium 11 (or in fluid communication with the right atrium 11). As described in more detail below, an inner movable member 140 of the catheter 120 can be adjusted (FIG. 3) relative to the outflow port 123 so as to occlude the coronary sinus 20 and thereby cause redistribution of the venous blood into the heart muscle tissue 30. Also, the inner movable member 140 can be positioned (FIG. 4) relative to the outflow port 123 so as to open a blood flow path from the coronary sinus 20 and to the right atrium 11. Accordingly, the control system 160 housed in the heart-lung machine 102 can be configured to adjust the position of the inner movable member 140 so as to provide intermittent occlusion of the coronary sinus 20 during different periods of the cardiac surgery. In such circumstances, the stabilization balloon device 122 can remain inflated in the coronary sinus occlusion catheter 120 during the cardiac surgery regardless of whether the coronary sinus is occluded or non-occluded.

Referring now to FIG. 1, the heart-lung machine 102 may include a number of components that provide the extracorporeal circuit for delivering oxygenated blood to the patient's circulatory system. For example, the heart-lung machine 102 may include a plurality of roller pumps 109, 110, 111, and 112 that can be individually activated and controlled to deliver a controlled flow of fluids, such as cardioplegia or blood. The heart-lung machine can also include an oxygenator circuit 115 having a blood reservoir tank, a centrifugal blood pump, a bubble remover, and a number of sensors. A first blood flow line 116 for delivering oxygenated blood can extend from the heart lung machine 102 and can be connected to the aorta 16. A second blood flow line 117 that returns venous blood to the heart-lung machine 102 can be connected to the superior vena cava 17, the inferior vena cava, or both. An internal control system of the heart lung machine (which may be separate from or incorporated with the control system 160) can be used to monitor the blood sensors and the patient's conditions so as to provide an ample supply of oxygenated blood to the patient's circulatory system when the heart 10 is clamped off from the circulatory system.

The proximal portion 131 of the coronary sinus occlusion catheter is positioned external to the patient while the distal tip portion 121 is advanced into the coronary sinus 20. The proximal portion 131 includes the proximal hub 132 that is coupled to the heart-lung machine 102 via a set of fluid or sensor lines 150, 153, 154, 155, 156, and 159. As such, the control system 160 housed in the heart-lung machine 102 can inflate or deflate the stabilization balloon 122 and also adjust the position of the inner movable member 140 while contemporaneously receiving a plurality of sensor signals that provide data indicative of heart characteristics (e.g., coronary sinus pressure, right atrial pressure of fluid flow, and the like).

In one example, the first line 150 extending between the control system 160 and the proximal hub 132 comprises an actuation line for adjusting the position of the inner movable member 140 at the distal portion 121 of the catheter 120. The first line 150 is connected to a corresponding port 101 of the heart-lung machine 102 so that the line 150 is connected with the control system 160 housed in the heart-lung machine 102. In some embodiments, the inner movable member 140 extends proximally from the distal portion 121 and through the proximal hub 132 and the actuation line 150 so that an actuator 165 (e.g., a pump, a motor, a magnetic actuator, a pneumatic actuator, or the like) housed in the heart-lung machine 102 can directly adjust the position of the inner movable member 140. Alternative, the proximal hub 132 can join the actuation line 150 with an actuation lumen 139 (FIG. 5) of the catheter 120 so that the actuator 165 housed in the heart-lung machine 102 can deliver an actuation force (e.g., via a fluid pressure force, a push-pull cable, an electric signal that generates a magnetic force at a coil along the distal portion, or the like) to drive the movement of the inner movable member 140.

In another example, the second line 153 extending between the control system 160 and the proximal hub 132 comprises an inflation-deflation line through which pressurized fluid (e.g., helium, another gas, or a stable liquid) can be delivered to inflate the stabilization balloon device 122 (and can be evacuated to deflate the balloon device 122). The inflation-deflation line 153 is connected to a corresponding port 103 of the inflation-deflation so that the line 153 is in fluid communication with a pneumatic subsystem of the control system 160 housed in the heart-lung machine 102. The proximal hub 132 joins the inflation-deflation line 153 with a balloon control lumen 133 (FIG. 5) extending through the coronary sinus occlusion catheter 120 to a set of ports at the interior of the balloon device 122.

In another example, the third line 154 extending between the heart-lung machine 102 and the proximal hub 132 comprises a balloon sensor line that is in fluid communication with the interior of the balloon device 122 so as to measure the fluid pressure within the balloon device 122. The proximal hub 132 joins the second line 154 with a balloon pressure-monitoring lumen 134 (FIG. 5) extending through the coronary sinus occlusion catheter 120 to a second set of ports at the interior of the balloon device 122. The pressure of the balloon device 122 may be monitored by the control circuitry 162 (FIG. 1) of the control system 160 as part of a safety feature that is employed to protect the coronary sinus 20 from an overly pressurized balloon device. The balloon sensor line 154 is connected to a corresponding port 104 of the heart-lung machine 102 so that a pressure sensor arranged within the control system 160 can detect the fluid pressure in the balloon device 122. Alternatively, a pressure sensor may be arranged in the distal tip portion 121 or in the proximal hub 132 such that only a sensor wire connects to the corresponding port 104 of the heart-lung machine 102.

The proximal hub 132 also connects with a fourth line 155 extending from the heart-lung machine 102. The fourth line 155 comprises a coronary sinus pressure line that is used to measure the fluid pressure in the coronary sinus 20 both when occluded and non-occluded. The proximal hub 132 joins the fourth line 155 with a coronary sinus pressure lumen 135 (FIGS. 5-6) extending through the coronary sinus occlusion catheter 120 and to the distal port 129 that is distally forward of the balloon device 122. As such, the coronary sinus pressure lumen 135 and at least a portion of the third line 155 may operate as a fluid-filled pressure transmission path (e.g., saline, another biocompatible liquid, or a combination thereof) that transfers the blood pressure in the coronary sinus 20 to a pressure sensor device 107 along a proximal portion of the fourth line 155. The pressure sensor device 107 samples the pressure measurements (which are indicative of the coronary sinus pressure) and outputs a sensor signal indicative of the coronary sinus pressure to the corresponding port 105 of the heart-lung machine 102 for input to the control system 160. The coronary sinus pressure data may be displayed by the graphical user interface 119 in a graph form so that a surgeon or other user can readily monitor the trend of the coronary sinus pressure while the coronary sinus 20 is in an occluded condition and in a non-occluded condition. Optionally, the graphical user interface 119 of the heart-lung machine 102 can also output a numeric pressure measurement on the screen so that the surgeon can readily view a maximum coronary sinus pressure, a minimum coronary sinus pressure, or both. In alternative embodiments, the pressure sensor device 107 can be integrated into the housing of the heart-lung machine 102 so that the fourth line 155 is a fluid-filled path leading up to the corresponding port 105, where the internal pressure sensor device (much like the device 107) samples the pressure measurements and outputs a signal indicative of the coronary sinus pressure. Alternatively, the lumen 135 may carry an optical fiber or wire that connects to a pressure sensing element positioned at the distal opening of the lumen 135. As such, the pressure sensing element can be exposed to the fluid pressure at the distal end of the lumen 135, and the optical fiber or wire can communicate the pressure sensor signal to the control system 160.

Figure 4:
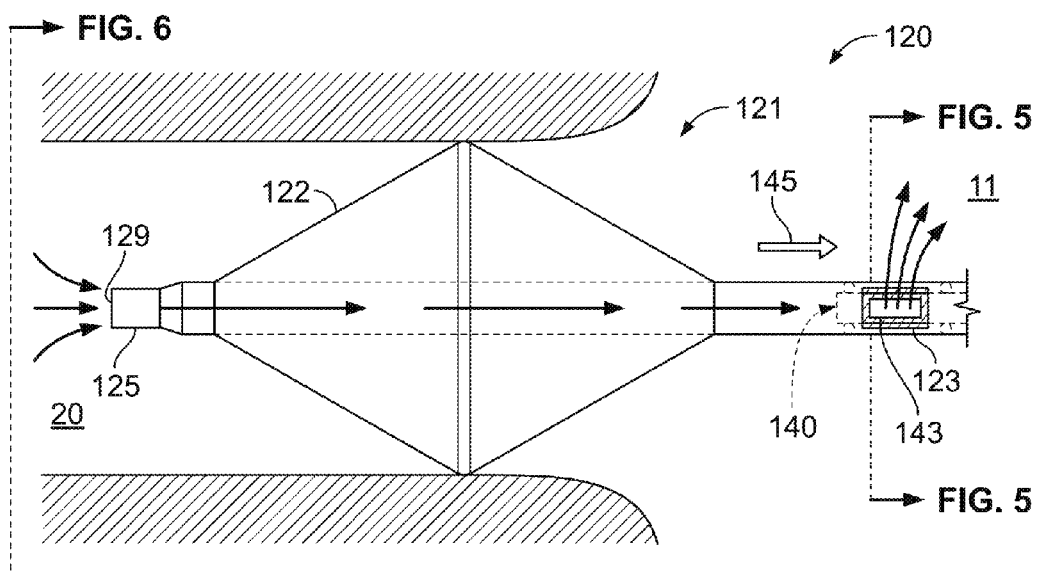
Figure 5:
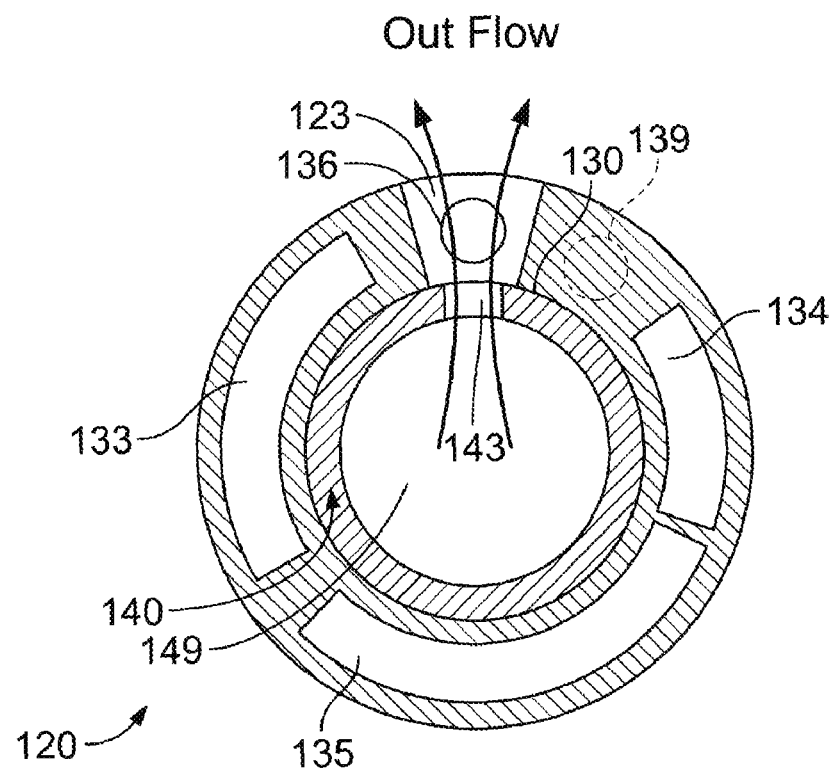
FIG. 5 is a cross-sectional view of a shaft portion the catheter device of FIG. 4.

In yet another example, the fifth line 156 extending between the heart-lung machine 102 and the proximal hub 132 comprises a sensor line that is employed to measure the fluid pressure or flow rate at the right atrium 11. The proximal hub 132 joins the fifth line 156 with an atrial sensor lumen 136 (FIG. 5) extending through the coronary sinus occlusion catheter 120 to a port that is exposed to the outflow port 123 proximal of the balloon device 122. In one example, the pressure in the right atrium (e.g., the fluid exiting the outflow port 123 into the right atrium) can be monitored by the control circuitry 162 (FIG. 1) of the control system 160 so as to determine the blood flow rate from the coronary sinus 20 into the right atrium 11. Namely, the pressure measured at the coronary sinus pressure lumen 135 (FIGS. 5-6) distally of the balloon device 122 can be compared to the pressure at the atrial sensor lumen 136 (FIG. 5) so as to determine the blood flow rate through the flow path when the inner movable member 140 is in a non-occluding position (FIG. 4). The fifth line 156 is connected to a corresponding port 106 of the heart-lung machine 102 so that a pressure sensor arranged within the control system 160 can detect the fluid pressure at the outflow port 123 located in the right atrium 11. Alternatively, a pressure sensor may be arranged in the distal end of the atrial sensor lumen 136 (FIG. 5) or the in the proximal hub 132 such that only a sensor wire connects to the corresponding port 106 of the heart-lung machine 102. For example, the lumen 136 may carry an optical fiber or wire that connects to a pressure sensing element positioned at the distal opening of the lumen 136 (FIG. 5). As such, the pressure sensing element can be exposed to the fluid pressure at the outflow port 123, and the optical fiber or wire can communicate the pressure sensor signal to the control system 160.

Figure 7:
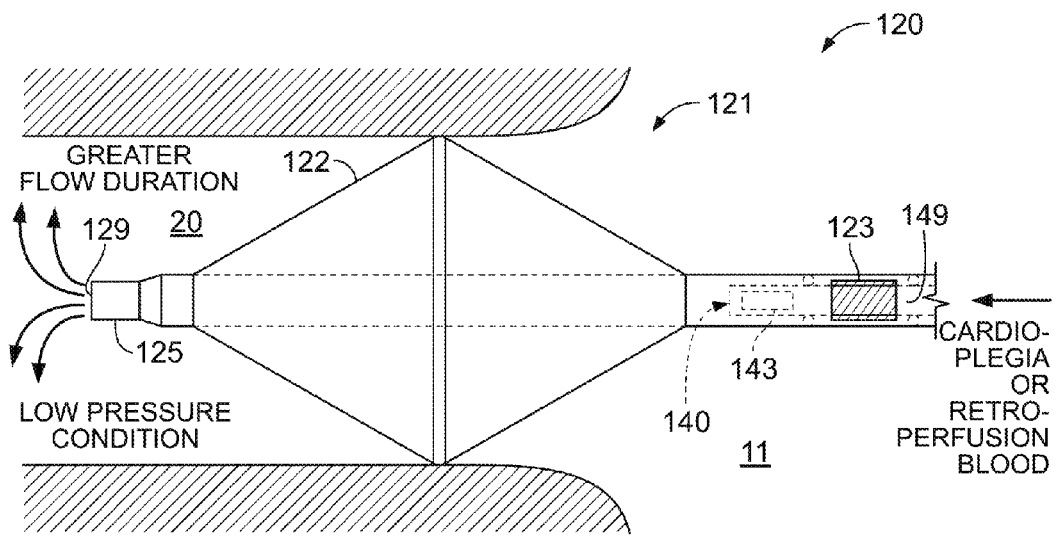
FIGS. 7-8 are side views of the distal portion of the catheter device of the system of FIG. 1, when delivering cardioplegia.
Figure 8:
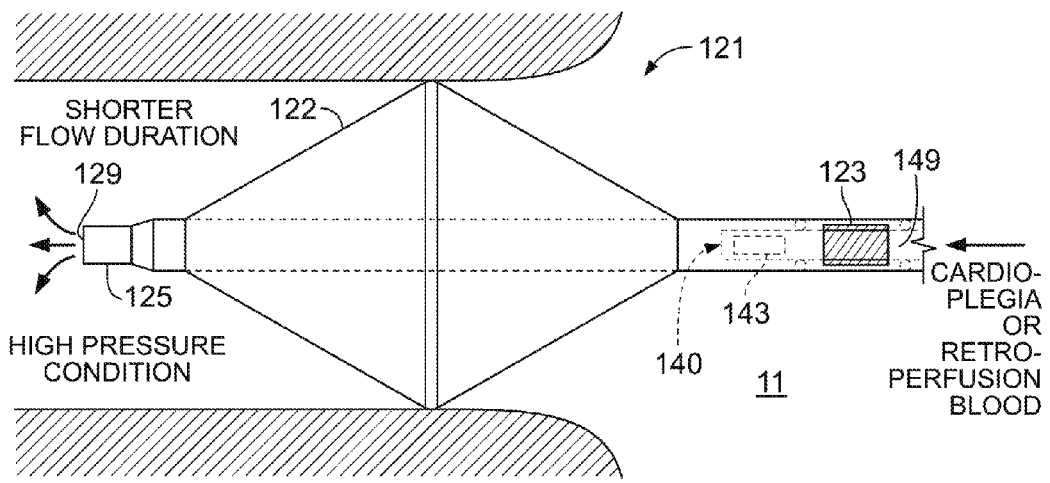

As shown in FIG. 1, in some embodiments a sixth line 159 may extend from the heart-lung machine 102 to the proximal hub so as to deliver cardioplegia, blood, or another fluid through the catheter 120 and out of the distal port 129 (FIGS. 7-8). The fluid line 155 can extend from one of the pumps 109, 110, 111, and 112 of the heart-lung machine 102 and may include a bubble-removal tank 118 that reduces or eliminates any bubbles in the fluid. The proximal hub 132 joins the sixth line 155 with the central lumen 130 (FIG. 5) which extends to the distal port 129 positioned distally of the balloon device 122. As such, the heart lung machine 102 can be operated to pump cardioplegia, blood, or another fluid through the central lumen 130 (FIG. 5) and out of the distal port 129 for retrograde cardioplegia treatment or retroperfusion of blood (described below) when the heart 10 is isolated from the circulatory system.

Optionally, the system 100 may include one or more ECG sensors to output ECG signals to the control system 160 housed in the heart-lung machine 102. For example, the ECG sensors can be connected to the control system 160 via a cable that mates with a corresponding port along the housing of the heart-lung machine 102. As described in more detail below, the ECG signals can be monitored during periods of the cardiac surgery both before and after the cardioplegia is delivered to the heart (e.g., while the heart is actively beating). The ECG data can be displayed by the graphical user interface 119 in a graph form so that a surgeon or other user can readily monitor the patient's heart rate and other characteristics (e.g., arterial pressure, aortic pressure, and the like) while the coronary sinus is in an occluded condition and in a non-occluded condition. Optionally, the graphical user interface 119 of the heart-lung machine 102 can also output numeric heart rate data based on the ECG sensor data on the screen so that the surgeon can readily view the heart rate (e.g., in a unit of beats per minutes). The ECG sensor signals that are received by the control system 160 are also employed by the control circuitry 162 (FIG. 1) so as to properly time the start of the occlusion period (e.g., the start time at which the inner movable member 140 is in the occlusion position (FIG. 3)) and the start of the non-occlusion period (e.g., the start time at which the inner movable member 140 is in the non-occlusion position (FIG. 4)).

As previously described, some embodiments of the control system 160 housed in the heart-lung machine 102 can include the control circuitry 162 having the pneumatics subsystem. The control circuitry 162 can include one or more processors that are configured to execute various software modules stored on at least one memory device (refer, for example, to FIG. 13). The processors may include, for example, microprocessors that are arranged on a motherboard so as to execute the control instructions of the control system 160. The memory device may include, for example, a computer hard drive device having one or more discs, a RAM memory device, that stored the various software modules (refer, for example, to FIG. 13). In some embodiments, the control circuitry 162 can be configured to activate the actuator unit 165 of the control system 160. As such, the control circuitry 162 can cause the actuator unit 165 to move the inner movable member 140 in a pattern based at least in part on the sensor signals indicative of the coronary sinus pressure (from the first sensor lumen 135 distal of the balloon device 122) and the right atrium pressure (from the second sensor lumen 136 proximal of the balloon device 122).

Figure 3:
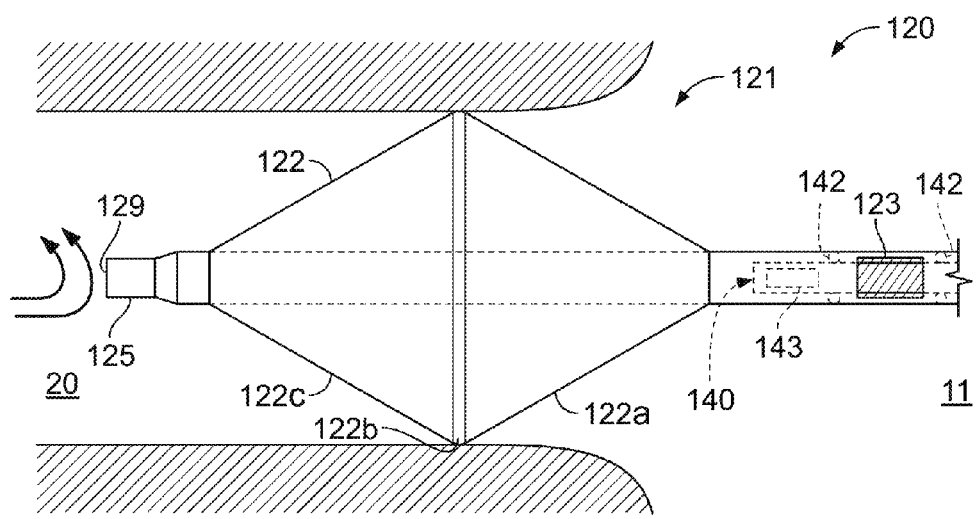
FIGS. 3-4 are side views of a distal portion of a catheter device of the system of FIG. 1, when intermittently occluding a vessel.

Referring now to FIGS. 3-4, the coronary sinus occlusion catheter 120 can be configured to intermittently occlude the coronary sinus 20 while the inflatable balloon device 122 remains inflated in the coronary sinus 20. The inflatable balloon device 122 of the coronary sinus occlusion catheter 120 may have a predetermined shape when in the inflated condition. In this embodiment, the inflatable balloon device 122 includes a first conical portion 122a narrowing down toward the distal direction, a second conical portion 122c narrowing down toward the proximal direction, and a small generally cylindrical rim portion 122b which is arranged between the conical portions. The narrowed ends of each of the conical portions 122a and 122c are connected with the catheter shaft so as to provide a seal that prevents gas leakage from the balloon device 122. In the inflated condition, the diameter of the balloon device 122 in the region of the cylindrical rim portion 122b is, for example, between about 12 mm and about 22 mm, and preferably about 15 mm. In some embodiments, the coronary sinus occlusion catheter 120 can be equipped with a marker band positioned inside the balloon device 122 and a second marker band near the distal port 129, each of which comprises an X-ray compatible material so as to be rendered visible during a surgery by suitable imaging processes.

As shown in FIG. 3, the inner movable member 140 of the catheter 120 can be arranged at a first position in which a fluid flow path between the distal port 129 and the outflow port 123 is blocked. As such, the coronary sinus 20 is in an occluded state when the inner movable member 140 is in the first position. The inner movable member 140 includes an opening 143 along a circumferential wall, which can be non-aligned with the outflow port 123 (refer to FIG. 3) or aligned with the outflow port 123 (refer to FIG. 4). When the opening 143 of the inner movable member 140 is offset from the outflow port 123 along the shaft of the catheter 120, the flow path between the distal port 129 and the outflow port 123 is blocked, thereby causing the venous blood flow in the coronary sinus 20 to be occluded. As such, the blood in the coronary sinus 20 is occluded from passing from the coronary sinus 20 to the right atrium 11. As previously described, this redistribution of the venous blood flow in the coronary sinus 20 can be employed to pre-condition the heart muscle tissue prior to delivering retrograde cardioplegia to the coronary sinus via the catheter 120. Further, the catheter device 120 can be used to limit the blood flow through the heart muscle tissue (draining from the coronary sinus 20 and into the right atrium 11) during the initial period after the heart 10 is reconnected to the circulatory system (after the heart is unclamped). The benefits from these procedures are described in more detail below.

As shown in FIG. 4, the position of the inner movable member 140 can be adjusted by a motion 145 so that the opening 143 is generally aligned with the outflow port 123 in the wall of the catheter 120. In such circumstances, the flow path between the distal port 129 and the outflow port 123 is opening, and blood is permitted to flow from the coronary sinus 20 and into the right atrium 11. As previously described, the movement of the inner movable member 140 in the catheter body can be controlled by be control system 160 housed in the heart-lung machine 102 (FIG. 1). For example, the actuator unit 165 of the control system 160 can provide a driving force that acts upon the inner movable member 140 to reciprocate the inner movable member between the first position (FIG. 3) and the second position (FIG. 4). The inner movable member 140 may slide along two or more seals 142 arranged inside the central lumen 130 (FIG. 5) of the catheter 120. (It should be noted that the seals 142 are not drawn to scale in FIGS. 3-4 and are enlarged for purposes of illustration.)

Accordingly, the inner movable member 140 can act as a valve that is positioned proximal to the stabilization balloon 122 and can be controlled to intermittently occlude the coronary sinus 20. Thus, while the stabilization balloon 122 remains continuously inflated in the coronary sinus 20, the inner movable member 140 can be controlled to intermittently move between the first position (FIG. 3) and the second position (FIG. 4) so as to cause the previously described redistribution of venous blood flow while also preventing the pressure in the coronary sinus from reaching unsafe levels. In particular embodiments, the control system 160 housed in the heart-lung machine 102 (FIG. 1) can actuate the inner movable member 140 according to one of two types of operations: (i) a predetermined pattern of intermittent coronary sinus occlusion (time periods are independent of coronary sinus pressure measurements), or (ii) a pressure-controlled intermittent coronary sinus occlusion (time periods are dependent upon the coronary sinus pressure measurements). For example, during an initial phase when the catheter 120 is first delivered into the coronary sinus 20 and initially activated to pre-condition the heart tissue prior to receiving cardioplegia, the control system 160 can cause the inner movable member 140 to reciprocate between the first and second positions according to the predetermined pattern of occlusion times and non-occlusion times. During these time periods in the initial phase, the coronary sinus pressure measurements are recorded by the control system 160 (and optionally displayed on the user interface display device 119), but the time periods for the occluded state and the non-occluded state are predetermined and do not change based upon the coronary sinus pressure measurements. After this initial phase, the control system 160 can automatically switch the second type of operation in which the time periods for the occluded state and the non-occluded state are a function of the previously recorded coronary sinus pressure measurements. For example, the control system 160 can cause the inner movable member 140 to reciprocate between the first and second positions according to a PICSO algorithm that assesses a previous set of coronary sinus pressure measurements to thereby determine the new time period for the next occluded state or non-occluded state.

Figure 6:
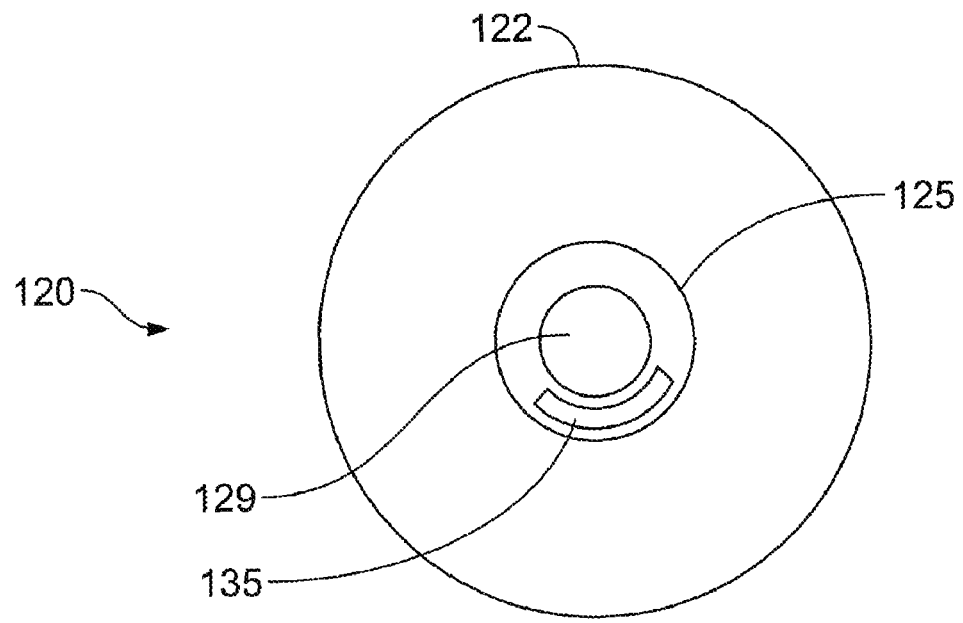
FIG. 6 is distal end view of a tip portion the catheter device of FIG. 4.

FIGS. 5 and 6 are different views of the distal portion 121 of the catheter 120 depicted in FIG. 4. As shown in the cross-section view of the outflow port 123 and the inner movable member 140 (FIG. 5), the shaft of the catheter 120 can include a plurality of lumens 130, 133, 134, 135, 136, and optionally 139. In this embodiment, the central lumen 130 extends from the proximal hub 132 (FIG. 1) to the distal port 129 (FIGS. 3-4) so as to provide fluid communication therethrough. The inner movable member 140 is positioned in the central lumen 130. For example, the inner movable member 140 can be a tubular piston device that is slidably positioned in the distal portion 121 of the catheter 120. In such circumstances, the catheter 120 may optionally include an actuator lumen 139 that extends from the proximal hub 132 (FIG. 1) in communication with the actuator line 150 (FIG. 1), so that the control system 160 can deliver an actuation force to the inner movable member (e.g., via a fluid pressure force such as an internal inflatable balloon that acts upon the inner movable member 140, a push-pull cable in the lumen 139 that that acts upon the inner movable member 140, an electric signal delivered via the lumen 139 that provides a magnetic force upon the inner movable member 140, or the like). In an alternative example, the inner movable member 140 may extend the entire length from the distal portion (refer to FIGS. 3-4) to the control system 160 in the heart-lung machine 102. As such, there may be no need for the actuator lumen 139, and the actuator unit 165 (FIG. 1) of the control system 160 may act upon a proximal end of the inner movable member 140. In each of the aforementioned embodiments, the inner movable member 140 may have a hollow tubular shape so that an inner lumen 149 permits fluid flowing from the fluid line 159 (FIG. 1) through the central lumen 130 (e.g., cardioplegia as shown in FIGS. 7-8) to pass through the inner movable member 140 toward the distal port 129. However, during the periods when the catheter 120 is used to intermittently occlude blood flow from the distal port 129 to the outflow port 123 (as previously described in connection with FIGS. 3-4), the fluid line 159 (FIG. 1) may be clamped at a proximal location so that the blood flows out from the outflow port 123 rather than advancing proximally through the central lumen 130 to the fluid line 159.

Still referring to FIG. 5, the inflation-deflation lumen 133 of the catheter 120 may be a ring segment-shaped lumen positioned radially outward of the central lumen 130. The inflation-deflation lumen 133 serves to supply and discharge fluid (e.g., helium gas in this embodiment) for inflating and evacuating the balloon device 122. Accordingly, the inflation-deflation lumen 133 may extend from the proximal hub 132 (FIG. 1) to a first set of ports located at the interior of the balloon device 122. The balloon pressure-monitoring lumen 134 may also be a ring segment-shaped lumen positioned radially outward of the central lumen 130. The balloon pressure-monitoring lumen 134 can be smaller than the inflation-deflation lumen 133 so that the ring segment-shaped lumens 133 and 134 are different in sized. The balloon pressure-monitoring lumen 134 extends from the proximal hub 132 to a second set of ports located at the interior of the balloon device 122 and serves to measure the fluid pressure within the balloon device 122.

As shown in FIGS. 5-6, the coronary sinus pressure lumen 135 in this embodiment is a ring segment-shaped lumen that extends fully to the distal end of the catheter 120. The lumen 135 may be filled with a biocompatible fluid that is in fluid communication with the fluid in the coronary sinus 20. Accordingly, the blood pressure in the coronary sinus 20 is transferred to the fluid-filled path extending through the lumen 135 and to the pressure sensor device 107 (FIG. 1). Alternatively, a miniature pressure sensor can be positioned at the distal end of the lumen 135 (FIG. 6) such that a sensor wire (e.g., electrical or optical) extends through the lumen 135 for communication with the control system 160 (FIG. 1).

Referring again to FIG. 5, the shaft of the coronary sinus occlusion catheter 120 includes the atrial sensor lumen 136, which is employed to measure either pressure or a flow rate at the outflow port 123, extending from the proximal hub 132 to a location adjacent to the outflow port 123. The flow rate passing through the outflow port 123 and into the right atrium 11 can be measured, for example, by detecting the fluid pressure at the outflow port 123. Then, the pressure measured at the coronary sinus pressure lumen 135 (distally of the balloon device 122) can be compared to the pressure at the atrial sensor lumen 136 (proximal of the balloon device 122) so as to determine the blood flow rate through the flow path when the inner movable member 140 is in a non-occluding position (FIG. 4). The atrial sensor lumen 136 may operate as a fluid-filled lumen such that the blood pressure acts upon and is transferred through the fluid in the lumen 136 for detection by a pressure sensor positioned outside the patient's body (e.g., incorporated in the heart-lung machine 102). Alternatively, a pressure sensor transducer may be arranged in the distal end of the atrial sensor lumen 136 (FIG. 5) such that only a sensor wire connects extends through the sensor lumen 136 to the corresponding port 106 of the heart-lung machine 102.

Referring now to FIGS. 7-8, the coronary sinus occlusion catheter 120 can be configured to deliver a treatment fluid such as cardioplegia or warm blood to the coronary sinus 20 while the inflatable balloon device 122 remains inflated in the coronary sinus 20. As shown in FIG. 7, the inner movable member 140 of the catheter 120 can be adjusted to the first position in which the inner movable member 140 blocks the outflow port 123 is blocked. In such circumstances, the fluid line 159 (FIG. 1) can be established or unclamped so that there is a delivery path from the fluid line 159, through the proximal hub 132, through the central lumen 130 and the inner lumen 149 of the inner movable member 140, and out of the distal port 129 into the coronary sinus 20. In some embodiments, the inner movable member 140 can be urged in the first position (in which the outflow port 123 is blocked) due to the treatment fluid passing through the lumen 130 of the catheter and driving the inner movable member 140 in the distal direction to block the outflow port 123. In such cases, the inner movable member 140 can be adjusted to the second position (to reopen the outflow port 123) when the heart-lung machine 120 temporarily vents blood or other fluid from the lumen 130 of the catheter 120 and thereby urges the inner movable member 140 in a proximal direction. In addition or in the alternative, the position of the inner movable member 140 can be controlled by the control system 160 before the treatment fluid is delivered through the lumen 130 and out of the distal port 129.

As previously described, the fluid that is dispensed into the coronary sinus 20 may be a cardioplegia solution, a warm blood supply that is used for retroperfusion (after cardioplegia delivery), or a pharmaceutical agent employed to treat the heart muscle tissue. Such a treatment fluid can be driven through the catheter 120 by one or more of the roller pumps 109, 110, 111, and 112 of the heart-lung machine. For example, the heart-lung machine 102 can be configured to deliver the cardioplegia into the coronary sinus at a rate of about 180 ml/min to about 220 ml/min, and preferably about the 200 ml/min. The time duration of the cardioplegia dispensation (and thus the amount of cardioplegia) can be at least partially based on the coronary sinus pressure measurements detected via the lumen 135 of the catheter 120. In another example, the heart-lung machine 102 can be configured to deliver warm blood supply (e.g., retroperfusion blood) into the coronary sinus at a rate of about 60 ml/min to about 470 ml/min, and preferably about 450 ml/min. The flow rate of the retroperfusion blood can be adjusted toward preferred rate of 450 ml/min, either manually or automatically under the control of the control system 160, based at least in part on a pressure sensor measurement from a pressure sensor at the bubble-removal tank 118 of the heart-lung machine 102.

In some embodiments, the control system 160 can be configured to automatically adjust the amount of the treatment fluid that is delivered into the coronary sinus 20 in response to the coronary sinus pressure data (e.g., the pressure sensor data from the lumen 135). For example, the heart-lung machine 102 can provide pulsatile retrograde cardioplegia into the coronary sinus 20 in response to the pressure measurements in the coronary sinus 20. This pressure-dependent process can be employed to control the amount of treatment fluid that is introduced into the coronary sinus 20 so that the retroinfusion amount will be neither too low nor too high. If the retroinfusion amount is too low, the venous pressure would be too low to ensure sufficient supply of the treatment fluid is passing to portion 30 of the heart muscle tissue that might otherwise develop into an ischemic region. If the retroinfusion amount is too high, the coronary venous pressure would increase at a substantial rate and entail the risk of an overperfusion and causing irreversible damage to the vessel walls.

FIGS. 7-8 illustrate one example of an automated control of the fluid delivery rate for the cardioplegia solution. In this example, the control system 160 is configured to automatically control of the amount of cardioplegia that is delivered through the catheter 120 and into the coronary sinus 20 as a function of at least one parameter derived from the coronary sinus pressure values measured via the lumen 135. For instance, if the pressure in the coronary sinus 20 is under a low pressure condition (FIG. 7), the time duration of the cardioplegia delivery (flowing at a constant 200 ml/min) may be relatively high so as to provide a high amount of cardioplegia flowing into the coronary sinus 20. If the pressure in the coronary sinus is in a high pressure condition, the time duration of the cardioplegia delivery (flowing at a constant 200 ml/min) may be relatively low so that a lesser amount of cardioplegia flows into the coronary sinus 20. In some embodiments, the pressure condition is not necessarily the absolute pressure measurements, but instead may be the time-derivative of the coronary sinus pressure measurements (e.g., the slope of the pressure curve). In such cases, if the time-derivative of the pressure measurement curve indicates that the pressure curve is rising at a higher rate (e.g., the pressure curve is not yet reaching a plateau level), the time duration of the cardioplegia delivery (flowing at a constant 200 ml/min) may be relatively high so as to provide a high amount of cardioplegia flowing into the coronary sinus 20. If the time-derivative of the pressure measurement curve indicates that the pressure curve is rising at a lower rate (e.g., the pressure curve is nearing a plateau level), the time duration of the cardioplegia delivery (flowing at a constant 200 ml/min) may be relatively low so that a lesser amount of cardioplegia flows into the coronary sinus 20.

Accordingly, the catheter 120 may serve a number of heart treatment functions after the stabilization balloon device 122 is inflated in the coronary sinus 20. As described in connection with FIGS. 3-4, the catheter 120 can be used to precondition heart muscle tissue before the heart is isolated (or clamped) from the circulatory system.

For example, the catheter 120 can provide PICSO treatment to the heart so as to precondition the heart muscle tissue with redistributed venous blood flow. As described in connection with FIGS. 7-8, the catheter 120 can be employed to deliver cardioplegia and/or a supply of warm blood into the coronary sinus during the cardiac surgery when the heart is isolated from the circulatory system. The rate at which the cardioplegia or supply of warm blood is delivered through the catheter 120 to the coronary sinus 20 can be controlled by the heart-lung machine 102 based at least in part upon pressure measurements of fluid in the coronary sinus 20. Furthermore, the catheter 120 can be employed to control the blood flow through the heart 10 after the heart 10 is reconnected (unclamped) with the circulatory system. Using the intermittent occlusion of the coronary sinus 20 as described in connection with FIGS. 3-4, the initial blood flow though the heart muscle tissue can be limited in a controlled manner that reduces the likelihood of damage to the heart muscle tissue that might otherwise occur if full normal blood flow was immediately restored (e.g., reducing and, in some cases, reversing reperfusion injury).

Figure 9:
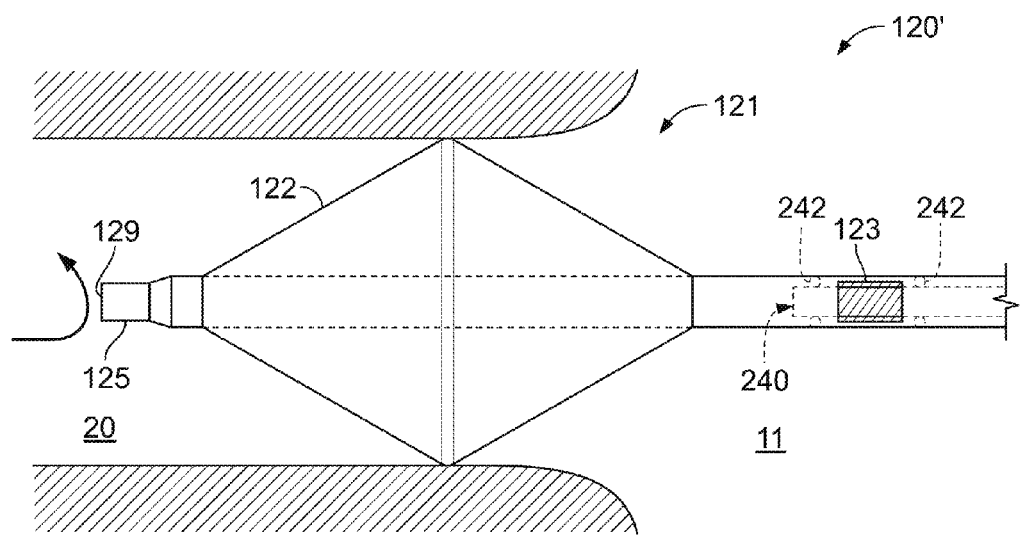
FIGS. 9-10 are side views of a distal portion of an alternative catheter device for use with the system of FIG. 1.
Figure 10:
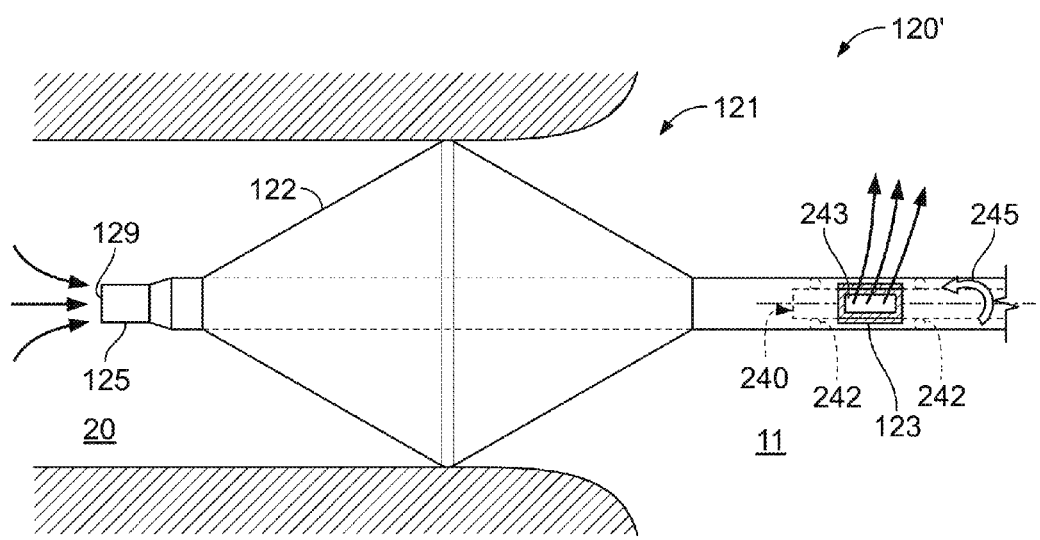

Referring now to FIGS. 9-10, some alternative embodiments of the coronary sinus occlusion catheter may include a different inner movable member 240 than that which was previously described in connection with FIGS. 3-4. For example, the alternative catheter 120' may be used with the heart-lung machine 102 as illustrated in FIGS. 1-2, but the inner movable member 240 may be configured to partially rotate within the catheter 120' (rather than longitudinally reciprocate). As shown in FIG. 9, the inner movable member 240 of the catheter 120' can be adjusted to a first position in which a fluid flow path between the distal port 129 and the outflow port 123 is blocked (because the inner movable member 240 blocks the port 123). As such, the coronary sinus 20 is in an occluded state when the inner movable member 240 is in the first position. The inner movable member 240 includes an opening 243 (FIG. 10) along a circumferential wall, which can be non-aligned with the outflow port 123 (refer to FIG. 9) or aligned with the outflow port 123 (refer to FIG. 10). When the opening 243 of the inner movable member 240 is offset from the outflow port 123, the flow path between the distal port 129 and the outflow port 123 is blocked, thereby causing the venous blood flow in the coronary sinus 20 to be redistributed. As previously described, this redistribution of the venous blood flow in the coronary sinus 20 can be employed to pre-condition the heart muscle tissue prior to delivering retrograde cardioplegia to the coronary sinus via the catheter 120'. Further, the catheter device 120' can be used to limit the blood flow through the heart muscle tissue (draining from the coronary sinus 20 and into the right atrium 11) during the initial period after the heart 10 is reconnected to the circulatory system (after the heart is unclamped).

As shown in FIG. 10, the inner movable member 240 can be rotated about its longitudinal axis by a rotational motion 245 so that the opening 243 is generally aligned with the outflow port 123 in the wall of the catheter 120'. In such circumstances, the flow path between the distal port 129 and the outflow port 123 is opened, and blood is permitted to flow from the coronary sinus 20 and into the right atrium 11. As previously described, the movement of the inner movable member 240 in the catheter body can be controlled by be control system 160 housed in the heart-lung machine 102 (FIG. 1). For example, the actuator unit 165 of the control system 160 can provide a driving force that acts upon the inner movable member 240 to rotate the inner movable member between the first position (FIG. 9) and the second position (FIG. 10). The inner movable member 240 may slidably rotate along two or more seals 242 arranged inside the central lumen of the catheter 120'. (It should be noted that the seals 242 are not drawn to scale in FIGS. 9-10 and are enlarged for purposes of illustration.)

Accordingly, the inner movable member 240 can act as a valve that is positioned proximal to the stabilization balloon 122 and can be controlled to intermittently occlude the coronary sinus 20. Thus, while the stabilization balloon 122 remains continuously inflated in the coronary sinus 20, the inner movable member 240 can be controlled to intermittently rotate between the first position (FIG. 9) and the second position (FIG. 10) so as to cause the previously described redistribution of venous blood flow while also preventing the pressure in the coronary sinus from reaching unsafe levels.

Figure 11:
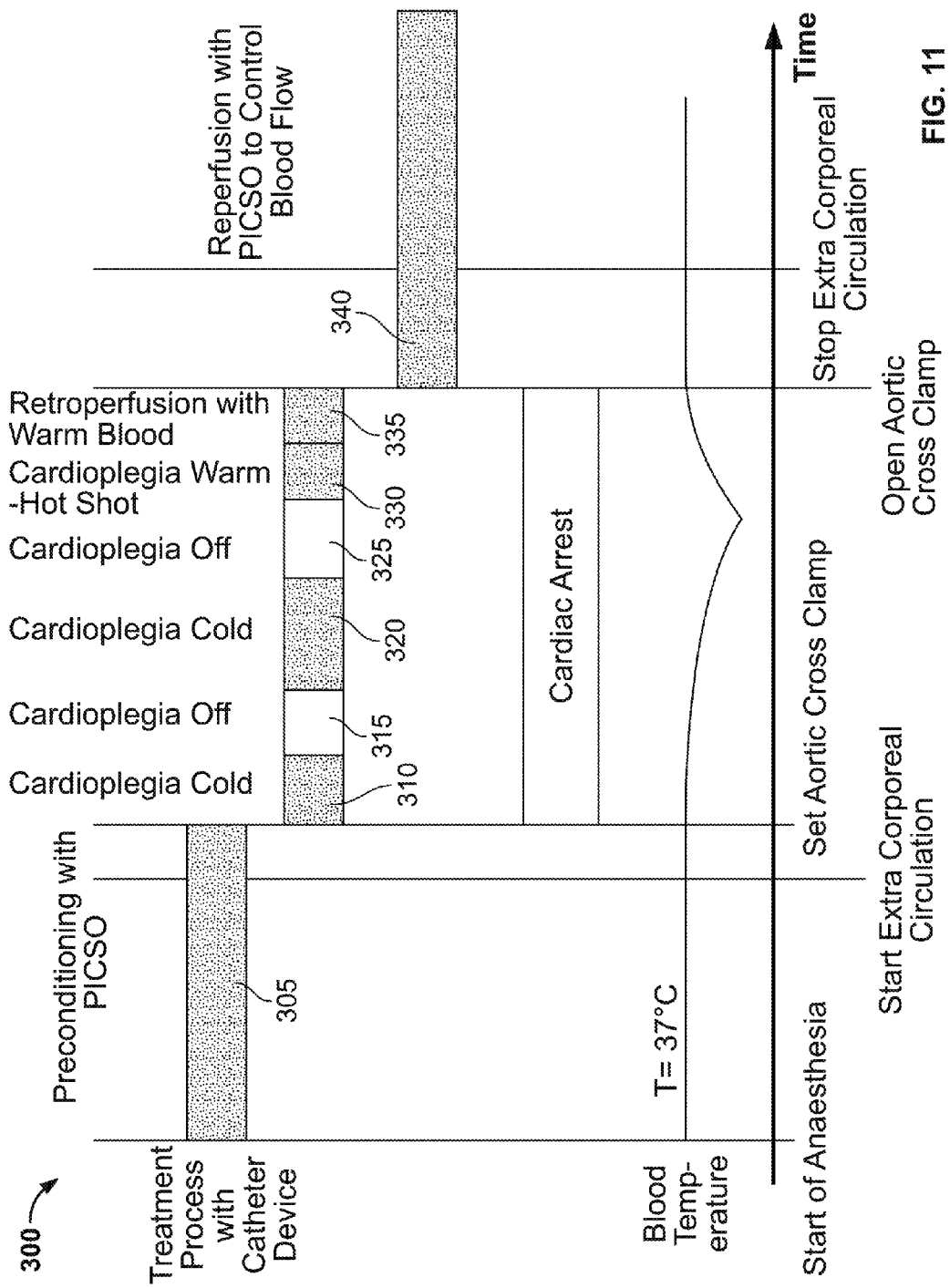
FIG. 11 is a chart of a process for treating heart tissue during a cardiac surgery, in accordance with some implementations.

Referring now to FIG. 11, a process 300 for treating heart tissue during a cardiac surgery can employ the previously described catheter 120 (or 120') in combination with a heart-lung machine 102. In particular, the catheter 120 (or 120') can be employed during a pre-conditioning phase of the process 300 before the heart 10 is isolated from the circulatory system (e.g., before the aortic cross clamp is applied). Second, the catheter 120 (or 120') can be used to deliver cardioplegia, a supply of warm blood, or both during a second phase of the process 300 in which the heart is isolated from the circulatory system. Thirdly, the catheter 120 (or 120') can also be used in a third phase of the process 300 after the heart 10 is reconnected to the circulatory system to restore normal blood flow (e.g., after the aortic cross clamp is opened).

As shown in FIG. 11, the process includes a step 305 of pre-conditioning the heart muscle tissue with a PICSO treatment. For example, the catheter 120 (or 120' can be used to provide PICSO treatment in which the coronary sinus 20 is intermittently occluded (e.g., occluded state, then non-occluded state, then occluded state, then non-occluded state, etc.) due to the movement of the inner movable member 140 (or 240). As described in connection with FIGS. 3-4 (or FIGS. 9-10), the control system 160 housed in the heart-lung machine 102 can control the adjustment of the inner movable member 140 (or 240) based at least in part on the coronary sinus pressure measurements detected via the lumen 135. This step 305 of pre-conditioning the heart muscle tissue with the PICSO treatment can be initiated after the start of anesthesia but before the extracorporeal circuit (refer to FIG. 1) is started. Further, this step 305 may continue for a period of time until the aortic cross clamp is set to thereby isolate the heart from the circulatory system.

After the heart 10 is isolated from the circulatory system, the process 300 may continue to a series of cardioplegia delivery steps 310, 315, 320, and 325. In this embodiment, a cold cardioplegia solution is delivered at steps 310 and 320 through the catheter 120 (or 120') for a period of time. As previously described in connection with FIGS. 7-8, the cardioplegia delivery may be a pulsatile retrograde cardioplegia delivery in which the rate of cardioplegia into the coronary sinus 20 is based at least in part on the coronary sinus pressure measurements detected via the lumen 135. Each period of cold cardioplegia delivery 310 and 320 is followed by a corresponding off period 315 and 325 in which no cardioplegia is delivered into the coronary sinus. During these steps 310, 315, 320, and 325, the cold cardioplegia solution may have a low temperature (e.g., about 4 degrees Celsius) so that the blood temperature of the heart 10 may be reduced. As a result, the heart 10 may stop actively beating (e.g., cardiac arrest) so that the surgeon may proceed to perform a primary surgical procedure such as a heart valve replacement or a coronary bypass procedure. It should be understood from the description herein that the process 300 is not limited to the series of two cold cardioplegia delivery steps 310 and 320, but instead may include a greater number of cold cardioplegia delivery steps in a larger series. Furthermore, in some embodiments, the process 300 may include a step of taking a blood sample from the heart 10 after the completion of each cardioplegia delivery step 310 and 320. The blood sample can be used to determine the presence of a number of characteristics that indicate whether there is a need for a further round or cardioplegia or other protection.

As shown in FIG. 11, the process 300 can include a step 330 of delivering a warm cardioplegia solution (e.g., a referred to herein as a "hot shot" of cardioplegia) through the catheter 120 (or 120') and into the coronary sinus 20 so as to initiate the process to warm the heart muscle tissue. The warm cardioplegia solution may have a relatively higher temperature (e.g., about 37 degrees Celsius) so that the blood temperature of the heart 10 may be increased. As previously described in connection with FIGS. 7-8, the warm cardioplegia delivery may be a pulsatile retrograde cardioplegia delivery in which the rate of warm cardioplegia into the coronary sinus 20 is based at least in part on the coronary sinus pressure measurements detected via the lumen 135.

In step 335, the process 300 includes delivering a supply of warm blood through the catheter 120 (or 120') and into the coronary sinus 20 so as to further the process of warming the heart muscle tissue. The warm blood may have a relatively higher temperature (e.g., about 37-38 degrees Celsius) so that the blood temperature of the heart 10 may be further increased toward the normal body temperature. As previously described in connection with FIGS. 7-8, the warm blood may be a pulsatile retrograde cardioplegia delivery in which the rate of warm cardioplegia into the coronary sinus 20 is based at least in part on the coronary sinus pressure measurements detected via the lumen 135.

After the heart 10 is reconnected to the circulatory system (e.g., after the aortic cross clamp is opened), the catheter device 120 (or 120') may remain in the coronary sinus 20 to provide further treatment to the heart 10. For example, the process 300 may include a step 340 of reperfusing the heart with blood flow from the circulatory system while the blood flow rate is limited or controlled using a PICSO treatment or (other intermittent occlusion) from the catheter 120 (or 120'). As described in connection with FIGS. 3-4 (or FIGS. 9-10), the control system 160 housed in the heart-lung machine 102 can control the adjustment of the inner movable member 140 (or 240) based at least in part on the coronary sinus pressure measurements detected via the lumen 135. As such, the full rate of normal blood supply is not applied to the heart muscle tissue when the heart 10 is reconnected with the circulatory system. Instead, the blood flow rate through the heart muscle tissue can be steadily increased or otherwise controlled so as to reduce the likelihood of damaging the heart muscle tissue with an immediate rush of blood flow from the arterial side. This step 340 of providing PICSO treatment after the heart 10 is reconnected to the circulatory system can continue for a period of time even after the extracorporeal circulation is stopped (e.g., the heart-lung machine 102 is no longer oxygenating the blood for the body).

Some embodiments of a system or method for treating heart tissue can include a multi-functional catheter device that provides a surgeon or other user with the ability to perform a number of heart treatment tasks (before, during, and after cardiac surgery) while a balloon device remains inflated in the coronary sinus. In particular, the catheter device can be readily used to precondition heart muscle tissue before the heart is isolated (or clamped) from the circulatory system. For example, the catheter device can be equipped to provide pressure-controlled intermittent coronary sinus occlusion (PICSO) treatment to the heart so as to precondition the heart muscle tissue with redistributed venous blood flow. Also, the catheter device can be employed to deliver cardioplegia (e.g., pulsatile retrograde cardioplegia in particular embodiments) into the coronary sinus during the cardiac surgery when the heart is isolated from the circulatory system. The pulsatile cardioplegia delivery can be used to dose the cardioplegia into the coronary sinus in an amount that is at least partially based upon pressure measurements in the coronary sinus. Furthermore, the catheter device can be employed to control the blood flow through the heart after the heart is reconnected (unclamped) with the circulatory system. As such, the initial blood flow though the heart muscle tissue can be limited in a controlled manner that reduces the likelihood of damage to the heart muscle tissue that might otherwise occur if full normal blood flow was immediately restored. Such treatment tasks provided by the catheter while the balloon is inflated in the coronary sinus can lead to improved heart muscle tissue recovery after the cardiac surgery is completed and arterial blood flow returns to the previously blood-deprived portion of the heart muscle tissue.

Accordingly, the process 300 depicted in FIG. 11 provides a surgeon or other user with the ability to perform a number of heart treatment tasks (before, during, and after cardiac surgery) while the balloon device 122 of the catheter 120 (or 120') remains continuously inflated in the coronary sinus 20. Before the start of the cardiac surgery (e.g., before the heart is isolated from the circulatory system), the catheter 120 (or 120') is used to precondition heart muscle tissue with a PICSO treatment to the heart (to precondition the heart muscle tissue with redistributed venous blood flow). During the cardiac surgery when the heart is isolated from the circulatory system, the catheter 120 (or 120') is used to deliver cardioplegia (e.g., pulsatile retrograde cardioplegia in particular embodiments) and (optionally) a supply of warm blood into the coronary sinus 20. After the cardiac surgery when the heart is reconnected (unclamped) with the circulatory system, the catheter 120 (or 120') can be employed to control the blood flow through the heart muscle tissue (which can protect the heart muscle tissue from potential damage). Such treatment steps provided by the catheter 120 (or 120') while the balloon device 122 is inflated in the coronary sinus 20 can lead to improved heart muscle tissue recovery after the cardiac surgery is completed and normal blood flow returns to the heart muscle tissue.

Figure 12:
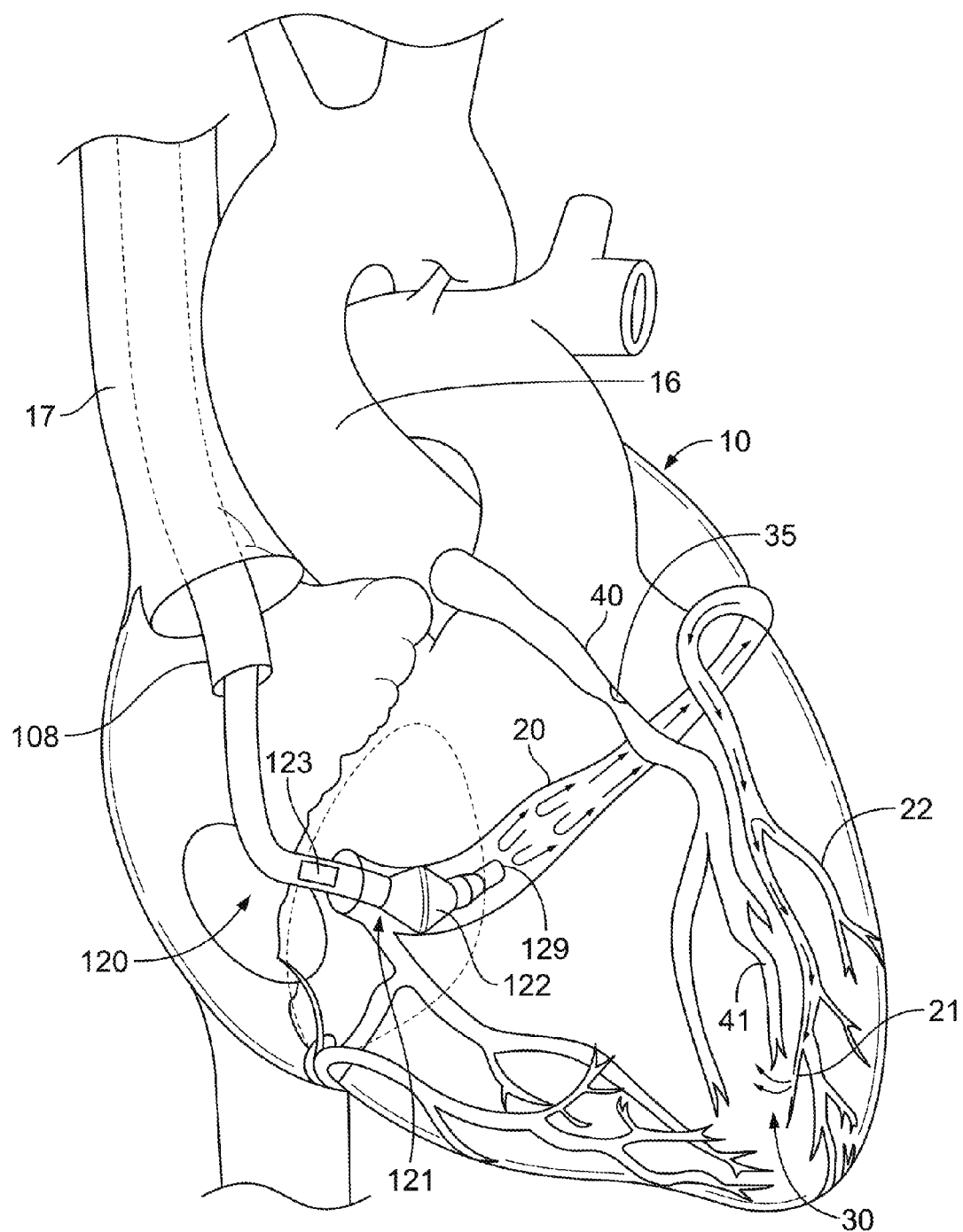
FIG. 12 is a perspective view of the catheter device of FIGS. 1-8, in an alternative system for use during an off-pump cardiac surgery or a PCI procedure.

Referring now to FIG. 12, some embodiments of the coronary sinus occlusion catheter 120 can be used in a PCI procedure or in an off-pump cardiac surgery in which the heart itself is providing the circulation (e.g., not a blood pump of a heart-lung machine). In these embodiments, the catheter can be used to intermittently occlude the coronary sinus 20 (e.g., by controlling the inner movable member 140 or 240 as described in FIGS. 3-4 or FIGS. 9-10). Moreover, the catheter 120 can be used to deliver retroperfusion blood into the coronary sinus 20 when the stabilization balloon device 122 remains in the inflated condition (similar to the embodiments depicted in FIGS. 7-8).

For example, when the catheter 120 is used in a PCI procedure, the catheter 120 may be delivered percutaneously through the venous system (e.g., through a guide member 108) and into the coronary sinus 20. The catheter 120 can provide PICSO treatment (by controlled movement of the inner movable member 140 or 240 as shown in FIG. 3-4 or 9-10) to the heart during the PCI procedure that is occurring in a different region of the heart. Also, during the PCI procedure, the lumen 130 of the catheter 120 that leads to the distal port 129 can be employed to selectively deliver retroperfusion blood into the coronary sinus 20. Such a feature may be useful, for example, during a PCI procedure in which a longer period of perfusion deficit may occur (e.g., during percutaneous valve procedures, during main stem stenting, or the like). The blood delivered through the lumen 130 of the catheter 120 and into the coronary sinus 20 may comprise arterial blood that is sampled from a major artery or an external source of oxygenated blood (e.g., a blood reservoir, an oxygenated blood tank from a perfusion machine, or the like). In some embodiments, the inner movable member 140 of the catheter 120 can be urged in the first position (in which the outflow port 123 is blocked as shown in FIG. 3) due to the retroperfusion blood passing through the lumen 130 of the catheter 120 and driving the inner movable member 140 in the distal direction to block the outflow port 123. In such cases, the inner movable member 140 can be adjusted to the second position (to reopen the outflow port 123) when some blood is vented from the lumen 130 of the catheter 120 to thereby urge the inner movable member 140 in a proximal direction. In addition or in the alternative, the position of the inner movable member 140 can be controlled by a control system (described below) before the retroperfusion blood is delivered through the lumen 130 and out of the distal port 129.

As shown in FIG. 12, the distal tip portion 121 of the coronary sinus occlusion catheter 120 can be arranged in a coronary sinus 20 of a heart 10 and thereafter activated to intermittently occlude the blood flow exiting from the coronary sinus 20 and into the right atrium 11. During such an occlusion of the coronary sinus 20, the venous blood flow that is normally exiting from the coronary sinus 20 may be redistributed into a portion of heart muscle tissue 30 that has been damaged due to blood deprivation or loss of functional myocardium. For example, the portion of heart muscle tissue 30 can suffer from a lack of blood flow due to a blockage 35 in a coronary artery 40. As a result, the arterial blood flow to the affected heart muscle tissue 30 via a local artery 41 can be substantially reduced such that the heart muscle tissue 30 becomes ischemic or otherwise damaged. In some embodiments, the coronary sinus occlusion catheter 120 can be delivered into the coronary sinus 20 and thereafter activated so as to intermittently occlude the coronary sinus 20 before, during, or after treating the blockage 35. Such an occlusion can cause the venous blood flow to be redistributed to the local vein 21 and then into the portion of heart muscle tissue 30 can suffer from a lack of blood flow due to a blockage 35 in a coronary artery 40. The ischemic or otherwise damaged heart muscle tissue 30 can receive the redistributed venous blood flow for an improved the supply of nutrients before, during, or after the blockage 35 is repaired or removed to restore normal coronary arterial blood flow.

In another example, when the catheter 120 is used in an off-pump cardiac surgery, the catheter 120 can be positioned in the coronary sinus 120 (e.g., preferably in a transatrial approach, but alternatively in a percutaneous delivery via a guide member 108) to provide PICSO treatment to the heart. In particular, the catheter 120 can provide the PICSO treatment by controlled movement of the inner movable member 140 or 240 as shown in FIG. 3-4 or 9-10. Further, the lumen 130 of the catheter 120 that leads to the distal port 129 can be used to selectively deliver retroperfusion blood into the coronary sinus (e.g., in the event of a sudden reduction in coronary sinus pressure). The blood delivered into the coronary sinus may comprise arterial blood that is sampled from a major artery or an external source of oxygenated blood. Such a process can be useful, for example, in cardiac surgeries when the heart is lifted in a pericardial cradle to allow surgical access to the posterior aspect of the heart (e.g., during coronary artery bypass in an off-pump cardiac surgery, or the like). As previously described, the inner movable member 140 of the catheter 120 can be urged in the first position (in which the outflow port 123 is blocked as shown in FIG. 3) due to the retroperfusion blood passing through the lumen 130 of the catheter 120 and driving the inner movable member 140 in the distal direction to block the outflow port 123. In such cases, the inner movable member 140 can be adjusted to the second position (to reopen the outflow port 123) when some blood is vented from the lumen 130 of the catheter 120 to thereby urge the inner movable member 140 in a proximal direction. In addition or in the alternative, the position of the inner movable member 140 can be controlled by a control system (described below) before the retroperfusion blood is delivered through the lumen 130 and out of the distal port 129.

In these embodiments in which the catheter 120 is employed in an off-pump cardiac surgery or a PCI procedure, the catheter 120 may be controlled by a control system that operates similarly to the control system 160 described in connection with FIG. 1. For example, the control system may receives the inputs from the pressure sensing lumens 135 and 136 and control the position of the inner movable member 140. The control system can be housed in a separate control module in the form of a workstation computer or laptop computer that receives the connections from catheter's proximal lines or can be housed in the heart-lung machine 102 as described in connection with FIG. 1 (even though the pumps of the heart-lung machine are not necessarily employed). As described in more detail below in connection with FIG. 13, the control system can include a computer processor 163 that executes computer-readable instructions stored on a computer memory device 166 or storage device 167 so as to activate or deactivate the occlusion in the coronary sinus 20 in accordance with particular patterns, which may be based at least in part upon the coronary sinus pressure measurements obtained via the lumen 135.

Figure 13:
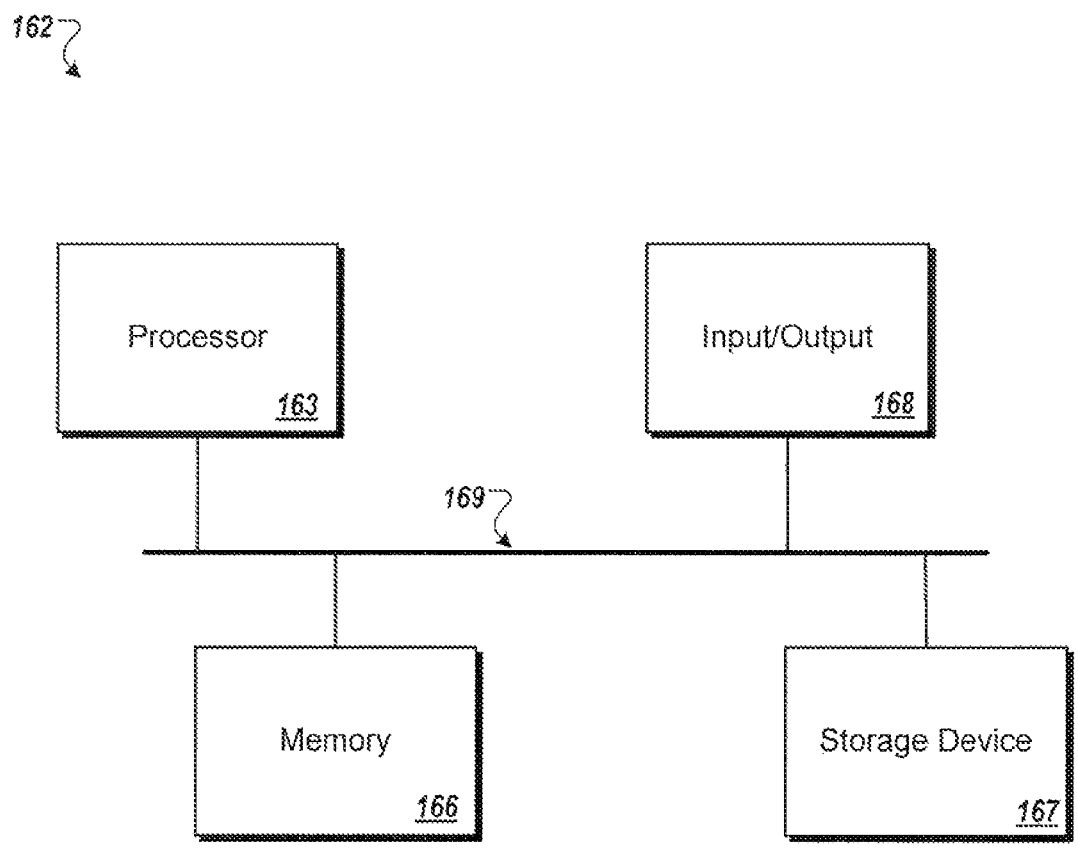
FIG. 13 is a diagram of a control circuitry for use in combination with a catheter device, in accordance with some embodiments.

Referring now to FIG. 13, as previously described, the control system for controlling the coronary sinus occlusion catheter (such as the control system 160 described in FIG. 1) can include control circuitry 162 having one or more processors that executed software modules stored on one or more memory devices. It should be understood from the description herein that the control system 160 (or at least he control circuitry 162) can be housed in a heart-lung machine 102 as described in FIG. 1 or alternatively can be housed in a separate control module have the form of a workstation computer or laptop computer. FIG. 13 is a block diagram of one example of the control circuitry 162 that may be used to implement the systems and methods described in this document. For example, the control circuitry 162 may be used in the heart-lung machine 102 (FIG. 1) or in a separate controller module in the form of a workstation computer or laptop computer having instructions dedicated for the control of the catheter 120. The control circuitry 162 includes a processor 163, memory 166, a storage device 167, input and output devices 168 for connecting to data entry devices and graphical displays, and a bus system 169 that provides for communications between these components. The processor 163 can process instructions for execution within the control circuitry 162, including instructions stored in the memory 166 or on the storage device 167 to perform various operations described previously in this document. In addition, the components described in this specification may also be implemented in firmware or on an application specific integrated circuit (ASIC), in which case this FIG. 13 diagram is simply illustrative of device operation. The control features described herein may be implemented in digital electronic circuitry, or in computer hardware, firmware, software, or in combinations of them. Also, the described control features may be implemented advantageously in one or more computer programs that are executable on a programmable system including at least one programmable processor coupled to receive data and instructions from, and to transmit data and instructions to, a data storage system, at least one input device, and at least one output device.

Figure 14:
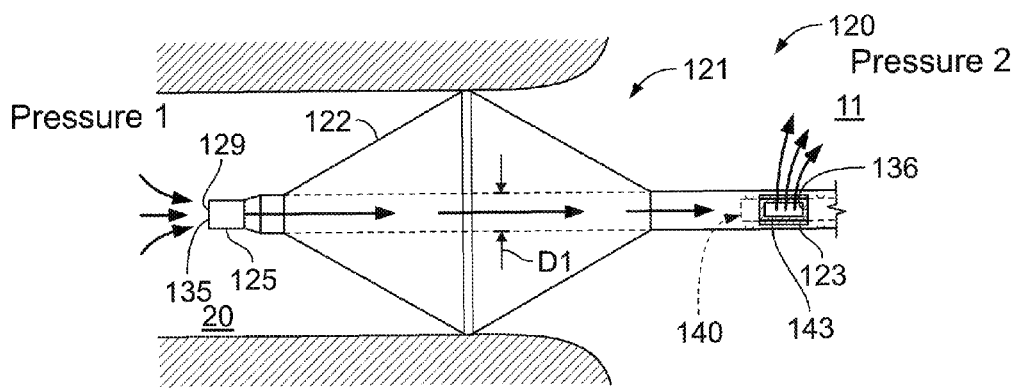
FIG. 14 is a side view of a distal portion of the catheter device of FIG. 4 used for intermittently occluding a vessel and determining a blood flow rate, in accordance with some embodiments.
Figure 15:
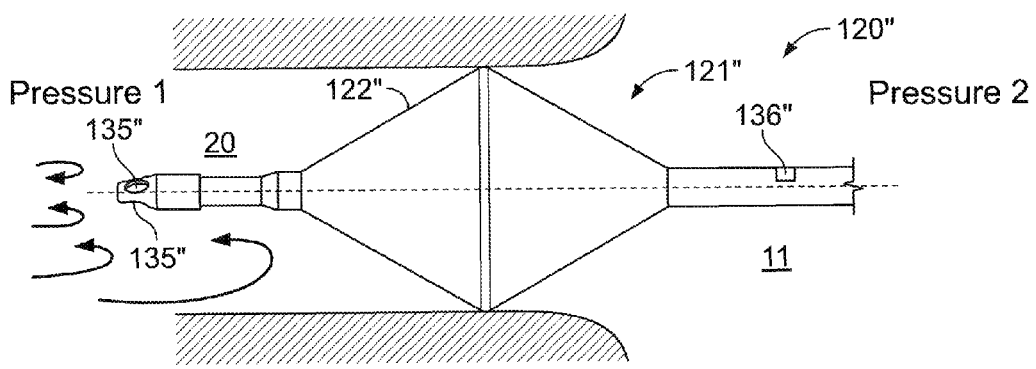
FIGS. 15-16 are side views of a distal portion of an alternative catheter device used for intermittently occluding a vessel and determining a blood flow rate, in accordance with particular embodiments.
Figure 16:
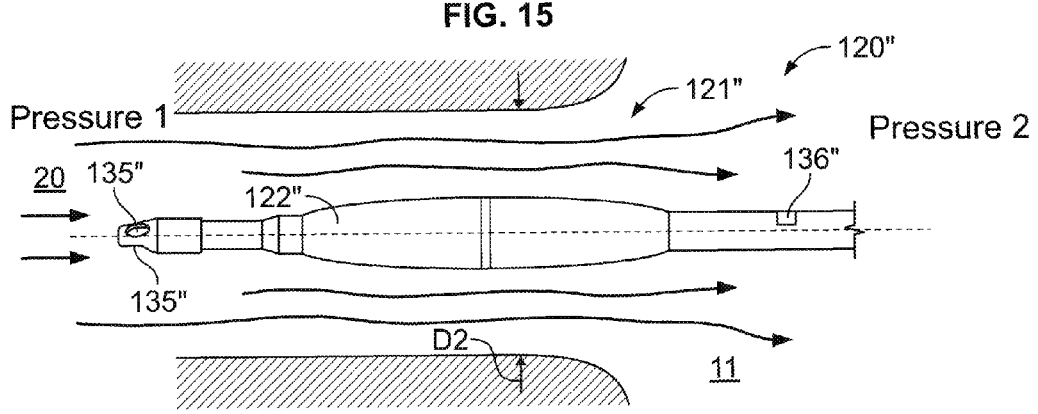

Referring now to FIGS. 14-16, some embodiments of the catheter device described herein can be configured to monitor a flow rate of blood passing from the coronary sinus 20 to the right atrium 11, in addition to providing the capability to intermittently occlude the coronary sinus 20 (e.g., PICSO treatment) or to deliver a treatment fluid (e.g., cardioplegia or retroperfusion blood) into the coronary sinus 20. FIG. 14 illustrate the embodiment of the catheter device 120 as previously described in connection with FIGS. 3-4 in which the inner movable member 140 enables the catheter device 120 to intermittently occlude the coronary sinus 20 (e.g., to provide PICSO treatment) while the inflatable balloon device 122 remains continuously inflated (e.g., a stabilization balloon). FIGS. 15-16 illustrate an alternative catheter device 120" in which the inflatable balloon device 122 is configured to intermittently adjust between a deflated condition (FIG. 16) and an inflated condition (FIG. 15) when positioned in the coronary sinus 20 so as to intermittently occlude the coronary sinus 20 (e.g., to provide PICSO treatment). In both embodiments, the catheter device 120 or 120" can be equipped with a first pressure sensor lumen 135 or 135" extending to a distal position that is distal of the inflatable balloon device 122 or 122"

(e.g. in the coronary sinus 20) and a second pressure sensor lumen 136 or 136" extending to a proximal position that is proximal of the inflatable balloon device 122 or 122" (e.g., in the right atrium 11). As described in more detail below, the first pressure sensor lumen 135 or 135" and the second pressure sensor lumen 136 or 136" are positioned relative to one another such that a difference between a first pressure (at 135 or 135") and a second pressure (at 136 or 136") is indicative of a flow rate of blood passing along the distal tip portion 121 or 121" from a region distal of the balloon device 122 or 122" to a region proximal of the balloon device 122 or 122".

As shown in FIG. 14, the catheter device 120 can include the distal tip portion 121 including the inflatable balloon device 122 configured to engage an interior wall of a coronary sinus 20 when in an inflated condition. As previously described in connection with FIGS. 1-4 and 12, the inflatable balloon device 122 operates as a stabilization balloon that is configured to remain continuously inflated when blood passes along the distal tip portion 121 from the region distal of the balloon device 122 (e.g., from the distal port 129 in the coronary sinus 20) to the region proximal of the balloon device 122 (e.g., to the outflow port 123 in the right atrium 11). The distal port 129 is arranged distally of the inflatable balloon device 122 so that the distal port 129 extends into the coronary sinus 20 when the inflatable balloon device 122 is inflated in the coronary sinus 20. The outflow port 123 is arranged proximally of the inflatable balloon device 122 so that the outflow port 123 is in fluid communication with the right atrium 11 when the inflatable balloon device 122 is inflated in the coronary sinus. Also as previously described in connection with FIGS. 1-4 and 12, the distal tip portion 121 in this embodiment at least partially defines a fluid flow path from the distal port 129 to the outflow port 123, and the inner movable member 140 can be positioned in the flow path so that the inner movable member 140 is adjustable between a first position in which the flow path from the distal port 129 to the outflow port 123 is occluded and a second position (shown in FIG. 14) in which the flow path is open.

The catheter device 120 can be equipped with first and second pressure sensing means for providing pressure data that is indicative of blood flow from the coronary sinus 20 into the right atrium 11. For example, the catheter device 120 can include the first pressure sensor lumen 135 (refer also to FIGS. 5-6) that extends to a position distal of the inflatable balloon device 122 for detecting a first pressure (e.g., a blood pressure in the coronary sinus 20). The catheter device 120 can also include a second pressure sensor lumen 136 (refer also to FIG. 5) extending to a position proximal of the inflatable balloon device 122 for detecting a second pressure (e.g., a blood pressure at the outflow port 123 into the right atrium 11). As shown in FIG. 14, the first pressure sensor lumen 135 and the second pressure sensor lumen 136 are positioned relative to one another such that a difference between the first pressure and the second pressure (e.g., ΔP) can be used as a parameter that is indicative a flow rate of blood passing along the distal tip portion 121 from the coronary sinus 20 to the right atrium 11.

For example, as shown in FIG. 14, the cross-section area of the flow path of the blood can be estimated from the diameter (D1) of the fluid lumen 130 passing through the interior of the balloon device 122. This cross-sectional area can be a predetermined value that is input into the control system for the catheter device 120. When the catheter device 120 is in the non-occluded state and blood is flowing through the distal portion of the fluid lumen and outward from the outflow port 123, the flow rate of the blood can be readily determined by the control circuitry 162 (previous described). For example, signals indicative of the first pressure at the first pressure sensor lumen (Pressure 1) and the second pressure at the second pressure sensor lumen 136 (Pressure 2) can be received by the control circuitry 162. From there, the control circuitry 162 can determine the blood flow rate based upon the cross-section area (known from the D1 measurement) and the pressure differential (ΔP=Pressure 1−Pressure 2). The flow rate value can be communicated to the user, for example on a display screen of the graphical user interface. This value for the volume flow rate can be useful during a cardiac surgery or during a PCI procedure because it can serves as an indicator or prognostic parameter for myocardial perfusion. In particular, a higher value for the volume flow rate may indicate that the myocardial perfusion is better (e.g., improved likelihood of patient survival).

As shown in FIGS. 15-16, some alternative embodiments of the alternative catheter device 120" can include an inflatable balloon device 122 that is configured to intermittently adjust between a deflated condition (FIG. 16) and an inflated condition (FIG. 15) when positioned in the coronary sinus 20 so as to intermittently occlude the coronary sinus 20 (e.g., to provide PICSO treatment). Similar to the previously described embodiments, the catheter device 120" can be equipped to measure the first pressure (distal of the balloon device 122" in the coronary sinus 20) and the second pressure (proximal of the balloon device 122" in the right atrium 11) so that the flow rate of blood passing from the coronary sinus 20 into the right atrium 11 can be determined and communicated to the user.

Similar to the previously described embodiments, the catheter device 120" can include the distal tip portion 121" including the inflatable balloon device 122" configured to engage an interior wall of a coronary sinus 20 when in an inflated condition. The catheter device 120" can also be equipped with first and second pressure sensing means for providing pressure data that is indicative of blood flow from the coronary sinus 20 into the right atrium 11. For example, the catheter device 120" can include a first pressure sensor lumen 135" (e.g., a central lumen having a plurality of distal ports at a distal end) that extends to a position distal of the inflatable balloon device 122" for detecting a first pressure (e.g., a blood pressure in the coronary sinus 20). The catheter device 120" can also include a second pressure sensor lumen 136" (e.g., a non-central lumen having one or more ports along the circumferential wall of the catheter shaft) extending to a position proximal of the inflatable balloon device 122" for detecting a second pressure (e.g., a blood pressure near the balloon 122" adjacent to the right atrium 11).

As shown in FIG. 15, when the balloon device 122" is in the inflated condition and engages the coronary sinus 20, the blood flow from the coronary sinus 20 to the right atrium 11 is occluded. Similar to previously described embodiments, the catheter device 120" can be coupled to a control system (having control circuitry 162) so as to intermittently adjust the balloon device 122" to intermittently occlude the coronary sinus 20 based at least partially upon the coronary sinus pressure (e.g., measured via the sensor lumen 135"). Thus, as the balloon repeatedly shifts from the deflated condition (FIG. 16) to the inflated condition (FIG. 15), the catheter device 120" is configured to provide PICSO treatment to the heart.

As shown in FIG. 16, the first pressure sensor lumen 135" and the second pressure sensor lumen 136" are positioned relative to one another such that a difference between the first pressure and the second pressure (e.g., ΔP) can be used as a parameter that is indicative a flow rate of blood passing along the distal tip portion 121" from the coronary sinus 20 to the right atrium 11. For example, the cross-section area of the flow path of the blood (when the balloon device 122" is deflated) can be estimated from the diameter (D2) of the coronary sinus 20 external to of the balloon device 122". This measurement D2 can be measured, for example, using an X-ray image, ultrasound imaging system, or other imaging system and then input into the control system for the catheter device 120". When the catheter device 120" is in the non-occluded state (FIG. 16) and blood is flowing along the distal portion 121", the flow rate of the blood can be readily determined by the control circuitry 162. As previously described, signals indicative of the first pressure at the first pressure sensor lumen (Pressure 1) and the second pressure at the second pressure sensor lumen 136 (Pressure 2) can be received by the control circuitry 162. From there, the control circuitry 162 can determine the blood flow rate based upon the cross-section area (known from the D1 measurement) and the pressure differential ($\Delta P$=Pressure 1−Pressure 2). The flow rate value can be communicated to the user, for example on a display screen of the graphical user interface. As previously described, this value for the volume flow rate can be useful during a cardiac surgery or during a PCI procedure because it can serves as an indicator or prognostic parameter for myocardial perfusion. In particular, a higher value for the volume flow rate may indicate that the myocardial perfusion is better (e.g., improved likelihood of patient survival).

Thus, in the embodiments described herein, the first pressure sensor lumen 135 or 135" can serve as a coronary sinus pressure lumen that extends to an opening arranged distally of the inflatable balloon device 122 or 122", and the second pressure sensor lumen 136 or 136" can serve as an atrial pressure sensor lumen that extends to an opening arranged proximally of the inflatable balloon device 122 or 122".

Further, it should be understood from the description herein that one or both of the first pressure sensor lumen 135 or 135" and the second pressure sensor lumen 136 or 136" is configured to be a fluid-filled pressure transmission path that transfers a blood pressure to a pressure sensor transducer (e.g., a pressure transducer positioned in the proximal hub 132 or incorporated into the control circuitry 162). Alternatively, one or both of the first pressure sensor lumen 135 or 135" and the second pressure sensor lumen 136 or 136" can include a miniature pressure sensor transducer positioned at a distal end of the respective lumen with an optical fiber or electric lead extending back through the lumen (e.g., for connection to the control circuitry 162).

A number of embodiments of the invention have been described. Nevertheless, it will be understood that various modifications may be made without departing from the scope of the invention. Accordingly, other embodiments are within the scope of the following claims.

What is claimed is:

1. A coronary sinus occlusion catheter, comprising:
   a distal tip portion including an inflatable balloon device configured to engage an interior wall of a coronary sinus when inflated;
   a distal port arranged distally of the inflatable balloon device so that the distal port extends into the coronary sinus when the inflatable balloon device is inflated in the coronary sinus;
   an outflow port arranged proximally of the inflatable balloon device and being continuously open so that the outflow port is in fluid communication with the right atrium when the inflatable balloon device is inflated in the coronary sinus, wherein the distal tip portion at least partially defines a fluid flow path from the distal port to the outflow port; and
   an inner movable member positioned in the flow path from the distal port to the outflow port, wherein the inner movable member is adjusted between a first position in which the flow path from the distal port to the outflow port is occluded and a second position in which the flow path from the distal port to the outflow port is open.

2. The catheter of claim 1, wherein the inner movable member comprises a hollow tubular member that defines an opening in a side wall of the hollow tubular member which is non-aligned with the outflow port when the inner movable member is in the first position and which is aligned with the outflow port when the inner movable member is in the second position.

3. The catheter of claim 2, wherein the inner movable member is repeatedly movable between the first position and the second position so as to intermittently open blood flow from the coronary sinus to the atrium when the inflatable balloon device remains continuously inflated against the interior wall of the coronary sinus.

4. The catheter of claim 2, wherein the inner movable member is longitudinally slidable relative to the outflow port when moving between the first position and the second position.

5. The catheter of claim 2, wherein the inner movable member is rotatable relative to the outflow port when moving between the first position and the second position.

6. The catheter of claim 2, wherein the inner movable member is adjusted between the first position and the second position by one of: (i) a magnetic force, (ii) a mechanical pusher, and (iii) a fluid force from a retroperfusion fluid passing through a lumen of the catheter and acting upon the inner movable member.

7. The catheter of claim 1, wherein the inner movable member is configured to intermittently adjust between the first position the second position so as to intermittently occlude the coronary sinus when the inflatable balloon device is inflated in the coronary sinus during an off-pump cardiac surgery.

8. The catheter of claim 7, further comprising a fluid delivery lumen extending from a proximal hub portion to the distal port that is arranged distally of the inflatable balloon device, wherein the fluid delivery lumen is configured to deliver retroperfusion blood into the coronary sinus when the inflatable balloon device is inflated in the coronary sinus during the off-pump cardiac surgery.

9. The catheter of claim 7, further comprising a fluid delivery lumen extending from a proximal hub portion to the distal port that is arranged distally of the inflatable balloon device, wherein the fluid delivery lumen is configured to deliver retroperfusion blood into the coronary sinus when the inflatable balloon device is inflated in the coronary sinus during the percutaneous coronary intervention procedure.

10. The catheter of claim 1, wherein the inner movable member intermittently is configured to intermittently adjust between the first position the second position so as to intermittently occlude the coronary sinus when the inflatable balloon device is inflated in the coronary sinus during a percutaneous coronary intervention procedure.

11. The catheter of claim 1, further comprising a proximal hub portion, a coronary sinus pressure lumen extending from the proximal hub portion to an opening that is arranged distally of the inflatable balloon device, an atrial sensor lumen extending from the proximal hub portion to an opening that is arranged proximally of the inflatable balloon device, and a balloon fluid lumen extending from the proximal hub portion to one or more openings that are arranged interior to the inflatable balloon device.

12. The catheter of claim 11, further comprising a balloon pressure-monitoring lumen extending from the proximal hub portion to one or more openings that are arranged interior to the inflatable balloon device.

13. The catheter of claim 11, further comprising a fluid delivery lumen extending from the proximal hub portion to the distal port that is arranged distally of the inflatable balloon device, wherein the fluid delivery lumen is configured to deliver cardioplegia or blood into the coronary sinus when the inflatable balloon device is inflated in the coronary sinus.

14. The catheter of claim 13, wherein the proximal hub portion is connectable to a plurality of fluid or sensor lines extending from a heart-lung machine.

15. A coronary sinus occlusion catheter, comprising:
    a distal tip portion including an inflatable balloon device configured to engage an interior wall of a coronary sinus when inflated;
    a proximal hub portion, a coronary sinus pressure lumen extending from the proximal hub portion to an opening that is arranged distally of the inflatable balloon device, an atrial sensor lumen extending from the proximal hub portion to an opening that is arranged proximally of the inflatable balloon device, and a balloon fluid lumen extending from the proximal hub portion to one or more openings that are arranged interior to the inflatable balloon device;
    a distal port arranged distally of the inflatable balloon device so that the distal port extends into the coronary sinus when the inflatable balloon device is inflated in the coronary sinus;
    an outflow port arranged proximally of the inflatable balloon device so that the outflow port is in fluid communication with the right atrium when the inflatable balloon device is inflated in the coronary sinus, wherein the distal tip portion at least partially defines a fluid flow path from the distal port to the outflow port; and
    an inner movable member positioned in the flow path from the distal port to the outflow port, wherein the inner movable member is adjusted between a first position in which the flow path from the distal port to the outflow port is occluded and a second position in which the flow path from the distal port to the outflow port is open.

16. The catheter of claim 15, further comprising a balloon pressure-monitoring lumen extending from the proximal hub portion to one or more openings that are arranged interior to the inflatable balloon device.

17. The catheter of claim 15, further comprising a fluid delivery lumen extending from the proximal hub portion to the distal port that is arranged distally of the inflatable balloon device, wherein the fluid delivery lumen is configured to deliver cardioplegia or blood into the coronary sinus when the inflatable balloon device is inflated in the coronary sinus.

18. The catheter of claim 17, wherein the proximal hub portion is connectable to a plurality of fluid or sensor lines extending from a heart-lung machine.

19. The catheter of claim 15, wherein the inner movable member comprises a hollow tubular member that defines an opening in a side wall of the hollow tubular member which is non-aligned with the outflow port when the inner movable member is in the first position and which is aligned with the outflow port when the inner movable member is in the second position.

20. The catheter of claim 19, wherein the inner movable member is repeatedly movable between the first position and the second position so as to intermittently open blood flow from the coronary sinus to the atrium when the inflatable balloon device remains continuously inflated against the interior wall of the coronary sinus.

21. The catheter of claim 19, wherein the inner movable member is longitudinally slidable relative to the outflow port when moving between the first position and the second position.

22. The catheter of claim 19, wherein the inner movable member is rotatable relative to the outflow port when moving between the first position and the second position.

23. The catheter of claim 19, wherein the inner movable member is adjusted between the first position and the second position by one of: (i) a magnetic force, (ii) a mechanical pusher, and (iii) a fluid force from a retroperfusion fluid passing through a lumen of the catheter and acting upon the inner movable member.

24. The catheter of claim 15, wherein the inner movable member is configured to intermittently adjust between the first position the second position so as to intermittently occlude the coronary sinus when the inflatable balloon device is inflated in the coronary sinus during an off-pump cardiac surgery.

25. The catheter of claim 24, further comprising a fluid delivery lumen extending from a proximal hub portion to the distal port that is arranged distally of the inflatable balloon device, wherein the fluid delivery lumen is configured to deliver retroperfusion blood into the coronary sinus when the inflatable balloon device is inflated in the coronary sinus during the off-pump cardiac surgery.

26. The catheter of claim 15, wherein the inner movable member intermittently is configured to intermittently adjust between the first position the second position so as to intermittently occlude the coronary sinus when the inflatable balloon device is inflated in the coronary sinus during a percutaneous coronary intervention procedure.

27. The catheter of claim 26, further comprising a fluid delivery lumen extending from a proximal hub portion to the distal port that is arranged distally of the inflatable balloon device, wherein the fluid delivery lumen is configured to deliver retroperfusion blood into the coronary sinus when the inflatable balloon device is inflated in the coronary sinus during the percutaneous coronary intervention procedure.

* * * * *